US010942196B2

(12) United States Patent
Malhotra et al.

(10) Patent No.: US 10,942,196 B2
(45) Date of Patent: Mar. 9, 2021

(54) SYSTEMS AND METHODS OF MOTION DETECTION USING DYNAMIC THRESHOLDS AND DATA FILTERING

(71) Applicant: Google Inc., Mountain View, CA (US)

(72) Inventors: Mark Rajan Malhotra, San Mateo, CA (US); Gwendolyn van der Linden, Redwood City, CA (US); Yash Modi, San Mateo, CA (US); Dongeek Shin, Mountain View, CA (US)

(73) Assignee: GOOGLE LLC, Mountain View, CA (US)

( * ) Notice: Subject to any disclaimer, the term of this patent is extended or adjusted under 35 U.S.C. 154(b) by 438 days.

(21) Appl. No.: 15/676,564

(22) Filed: Aug. 14, 2017

(65) Prior Publication Data

US 2019/0049479 A1    Feb. 14, 2019

(51) Int. Cl.
*G01P 13/00*    (2006.01)
*G01P 15/00*    (2006.01)
(Continued)

(52) U.S. Cl.
CPC ............... *G01P 13/00* (2013.01); *A61B 5/11* (2013.01); *A61B 5/721* (2013.01); *G01P 15/00* (2013.01);
(Continued)

(58) Field of Classification Search
CPC . G01P 13/00; G01P 15/00; A61B 5/11; A61B 5/721; A61B 5/0002; A61B 2562/0219; G06K 9/00342; G06K 9/00543
(Continued)

(56) References Cited

U.S. PATENT DOCUMENTS

| 4,845,464 A * | 7/1989 | Drori .................. B60R 25/1004 340/429 |
| 6,215,115 B1 * | 4/2001 | Baker .................. G01S 3/7864 250/214 C |

(Continued)

FOREIGN PATENT DOCUMENTS

WO    WO-2015157458 A1 * 10/2015    ........... G06F 17/141

OTHER PUBLICATIONS

Jin (X. Jin and et al, "Target Detection and Classification Using Seismic and PIR Sensors", IEEE Sensors Journal, vol. 12, No. 6, Jun. 2012) (Year: 2012).*

(Continued)

*Primary Examiner* — Alexander Satanovsky
*Assistant Examiner* — Douglas Kay
(74) *Attorney, Agent, or Firm* — Butzel Long

(57) ABSTRACT

Systems and methods of detecting human movement with a sensor are provided, including generating a motion event signal in response to movement detected by the sensor, and generating a parameterized curve to represent the detected motion. The parameterized curve is fit to a predetermined window of sensor data captured by the sensor to filter the motion event signal. A noise magnitude estimate and a curve fit error is determined based on the fitted parameterized curve to the predetermined window. A detection threshold value is determined based on the curve fit error, a noise source signal estimate of known noise, and zero or more noise magnitudes from other sources. Human motion is determined by correlating a true motion event signal with human motion based on a comparison between a value of a point on the parameterized curve and the detection threshold value.

20 Claims, 18 Drawing Sheets

(51) Int. Cl.
*G06K 9/00* (2006.01)
*A61B 5/00* (2006.01)
*A61B 5/11* (2006.01)

(52) U.S. Cl.
CPC ..... *G06K 9/00342* (2013.01); *G06K 9/00543* (2013.01); *A61B 5/0002* (2013.01); *A61B 2562/0219* (2013.01)

(58) Field of Classification Search
USPC .......................................................... 702/41
See application file for complete search history.

(56) References Cited

U.S. PATENT DOCUMENTS

| | | | | |
|---|---|---|---|---|
| 6,526,394 | B2* | 2/2003 | Baker | G01S 3/7864 706/4 |
| 8,674,831 | B1* | 3/2014 | Merrill | G08B 25/004 340/541 |
| 8,680,991 | B2 | 3/2014 | Tran | |
| 9,002,526 | B2 | 4/2015 | Matsuoka et al. | |
| 9,189,751 | B2 | 11/2015 | Matsuoka et al. | |
| 9,223,031 | B2* | 12/2015 | Burr | G01T 1/1647 |
| 9,495,975 | B2* | 11/2016 | Short | G01S 13/88 |
| 9,728,182 | B2* | 8/2017 | Short | G10L 25/03 |
| 10,376,670 | B2* | 8/2019 | Shouldice | A61B 5/486 |
| 10,410,623 | B2* | 9/2019 | Short | G10L 25/21 |
| 10,497,381 | B2* | 12/2019 | Short | G10L 13/02 |
| 2001/0021905 | A1* | 9/2001 | Burnett | A61B 5/0507 704/233 |
| 2002/0084414 | A1* | 7/2002 | Baker | G01S 3/7864 250/336.1 |
| 2008/0218361 | A1 | 9/2008 | Parker et al. | |
| 2009/0027648 | A1 | 1/2009 | Van Der Wijst | |
| 2010/0152600 | A1* | 6/2010 | Droitcour | A61B 5/05 600/534 |
| 2010/0214103 | A1 | 8/2010 | Egan et al. | |
| 2010/0240999 | A1* | 9/2010 | Droitcour | A61B 5/05 600/453 |
| 2011/0312285 | A1* | 12/2011 | Amir | H04W 52/0245 455/69 |
| 2015/0186312 | A1* | 7/2015 | Kim | G06F 13/4027 710/263 |
| 2015/0301513 | A1* | 10/2015 | Sager | H04Q 9/00 700/90 |
| 2016/0011053 | A1 | 1/2016 | Katz | |
| 2016/0116343 | A1* | 4/2016 | Dixon | G01J 1/44 250/342 |
| 2016/0189531 | A1* | 6/2016 | Modi | G08B 29/185 340/506 |
| 2016/0287180 | A1* | 10/2016 | Ansari | A61B 8/5269 |
| 2017/0003376 | A1 | 1/2017 | Wellman et al. | |
| 2017/0131336 | A1* | 5/2017 | Nelsen | G01R 31/001 |

OTHER PUBLICATIONS

F.C. Robertson and et el, "Motion Artifact Removal for Functional Near Infrared Spectroscopy: A Comparison of Methods", IEEE transactions on biomedical engineering, vol. 57, No. 6, Jun. 2010 (Year: 2010).*

Y. Zheng and et al, "Detecting Radio Frequency Interference for CSI Measurements on COTS WiFi Devices", IEEE ICC 2017 Ad-Hoc and Sensor Networking Symposium, May 2017 (Year: 2017).*

A. Godfrey and et al, "Direct measurement of human movement by accelerometry", Medical Engineering & Physics 30 (2008) 1364-1386 (Year: 2008).*

* cited by examiner

SYSTEMS AND METHODS OF MOTION DETECTION USING DYNAMIC THRESHOLDS AND DATA FILTERING

BACKGROUND

Detecting human motion using ambient motion sensors is difficult because of noise sources that exist in a detection environment (i.e., external noise sources), and because of noise sources within the sensor itself (i.e., internal noise sources). External noise sources include: airflow from HVAC (heating ventilation and air condition system) systems; electromagnetic interference (EMI) from mobile phones, electronic devices, wireless access points, or microwaves; electrostatic discharge (ESD) from dry air; and jarring due to movement of the sensor. Examples of internal noise sources are radio frequency (RF) induced currents due to wireless radio transmissions, and switching electronic components that generate internal currents and/or heat such as LEDs (light emitting diodes).

BRIEF SUMMARY

According to an implementation of the disclosed subject matter, a method is provided for detecting human movement with a sensor of a device, the method includes generating, at the sensor, a motion event signal in response to movement detected by the sensor. A parameterized curve may be generated, at a processor of the device coupled to the sensor, to represent the detected motion at the sensor based on the motion event signal. The parameterized curve may be fitted, at the processor, to a predetermined window of sensor data captured by the sensor that includes at least a portion of the motion event signal. A noise source signal magnitude estimate of a known noise may be determined at the processor based on the fitted parameterized curve to the predetermined window. A curve fit error may be determined at the processor based on the fitted parameterized curve to the predetermined window. A detection threshold value may be determined, at the processor, based on the curve fit error, the noise source signal estimate of the known noise, and zero or more noise magnitudes estimated at the processor from other sources. Human motion may be determined by correlating an estimated true motion event signal with human motion at the processor based on a comparison between a value of a point on the fitted parameterized curve and a detection threshold value.

According to an implementation of the disclosed subject matter, a system is provided that includes a sensor of a device to generate a motion event signal in response to movement detected by the sensor. The system includes a processor of the device, which is coupled to the sensor, to generate a parameterized curve to represent the detected motion at the sensor based on the motion event signal. The processor may fit the parameterized curve to a predetermined window of sensor data captured by the sensor that includes at least a portion of the motion event signal to filter the motion event signal. The processor may determine a noise source signal magnitude estimate of a known noise based on the fitted parameterized curve to the predetermined window. The processor may determine a curve fit error based on the fitted parameterized curve to the predetermined window. The processor may determine a detection threshold value based on the curve fit error, the noise source signal estimate of the known noise, and zero or more noise magnitudes estimated at the processor from other sources. The processor may determine that an estimated true motion event signal correlates with human motion based on a comparison between a value of a point on the parameterized curve and the detection threshold value.

According to an implementation of the disclosed subject matter, a system is provided that includes a processor of a device having a curve fit filter to receive an motion event signal from a sensor of the device, to output a filtered motion event signal based on the received motion event signal, and to determine a curve fit error. The processor may include a dynamic threshold estimator to output a detection threshold value based on the determined curve fit error from the curve fit filter, a noise source signal estimate of a known noise in the filtered motion event signal, and zero or more noise magnitude estimates from other sources. The processor may include a detector to output a determined motion event based on the filtered motion event signal from the curve fit filter and the detection threshold value from the dynamic threshold estimator.

According to an implementation of the disclosed subject matter, a method is provided that includes receiving, at a curve fit filter of a processor of a device, a motion event signal from a sensor of the device. A filtered motion event signal may be output, at the curve fit filter of the processor, based on the received motion event signal. The curve fit filter may determine a curve fit error. The method may include outputting, at a dynamic threshold estimator of the processor, a detection threshold value based on the determined curve fit error, a noise source signal estimate of a known noise in the filtered motion event signal, and on zero or more noise magnitude estimates. The method may include outputting, at a detector of the processor, a determined motion event based on the filtered motion event signal from the curve fit filter and the threshold value from the dynamic threshold estimator.

Additional features, advantages, and implementations of the disclosed subject matter may be set forth or apparent from consideration of the following detailed description, drawings, and claims. Moreover, it is to be understood that both the foregoing summary and the following detailed description are illustrative and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of implementations of the disclosed subject matter. No attempt is made to show structural details in more detail than may be necessary for a fundamental understanding of the disclosed subject matter and various ways in which it may be practiced.

DETAILED DESCRIPTION

Figure 1:
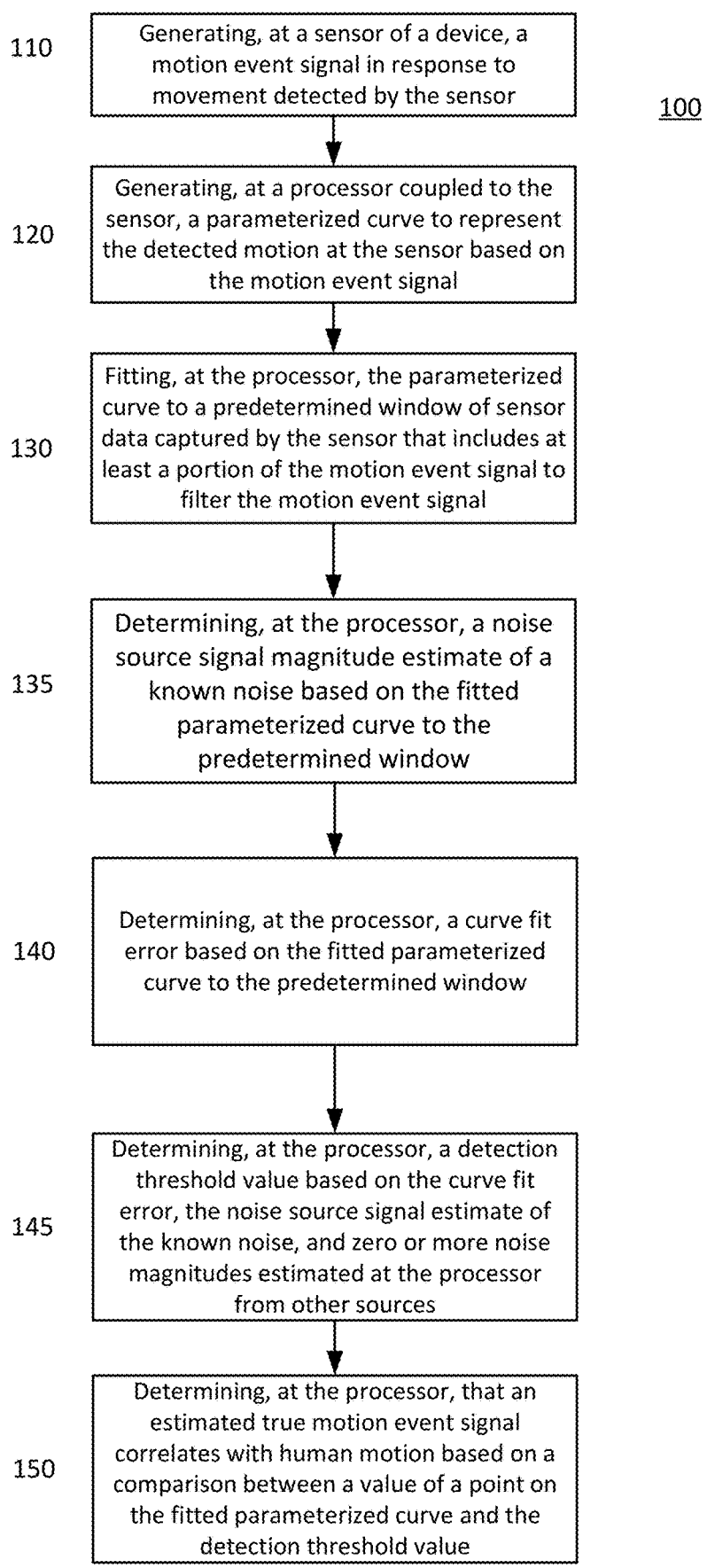
FIG. 1 shows a method of detecting human movement with a sensor of a device according to an implementation of the disclosed subject matter.

In implementations of the disclosed subject matter, one or more types of noise may be identified, and used to dynamically adjust a motion threshold of the sensor. Identified noise may be filtered from a motion event signal captured by a sensor so that a determination may be made as to whether there is a human motion event (e.g., walking). Different types of noise may have characteristic time signatures that may be identified and compensated for. When the type of noise is identified, a portion of the motion event signal detected by the sensor may be identified and determined to correspond to human movement. If the type of noise is only partially identifiable, it may be determined how much uncaptured noise may be expected, and the shape and/or profile of the noise as a function of time. A threshold of the sensor may be adjusted so that a human motion event may be determined from the detected motion event signal that may include noise. The total amount that the threshold value is raised may be based on the sum of individually identified noise signals.

Implementations of the disclosed subject matter determine whether there is a human motion event using one or more parameterized curves. By fitting the curves to a window of collected sensor data using parameter optimization techniques, the detected motion event signal may be separated into a human motion event signal and one or more noise signals, as well as a curve fit error. That is, a noise magnitude estimate and a curve fit error may be used to determine that the motion event signal correlates with human motion. The fitted human motion event component may be used for detection by taking the value of a specific point on the curve and by comparing it to the threshold value.

Implementations of the disclosed subject address the problems of present sensor systems, where the magnitude of the noise may be equal to or larger than a portion of the motion event signal that may correlate with a human motion event (e.g., human walking) in a detection range (e.g., at the edge of a detection range). This noise magnitude typically makes it difficult to determine human movement (e.g., human walking) in a motion event signal detected by a sensor. The systems and methods disclosed herein determine if a human is walking in the field-of-view of the sensor (e.g., a true positive), or whether sensor signals are solely due to noise (e.g., a true negative), based on the characteristics of the sensor signals.

The systems and methods of the disclosed subject matter determine the shape of motion event signals from one or more sensors in response to human movement detected by the one or more sensors is modeled using the parameterized curve. For example, a low-order polynomial or a sum of sinusoids over a limited frequency range may be used to model the parameterized curve. Noise signals, which may detected as part of the motion event signals detected by the one or more sensor, can be parameterized. For example, the noise signals may be parameterized as steps of spikes. By fitting these curves to a window of the collected sensor data (e.g., the last 10 samples, the last 20 samples, the last 50 samples, or the like) using parameter optimization techniques, such as least-squares, the motion event signal can be decomposed into signals representing human motion (e.g., a human walk event), one or more noise signals, and a remaining curve fit error. That is, the motion event signal from the sensor may include signal portions which may be curve fit to a human motion event and/or noise. The remaining portions of the motion event signal may be determined to be a remaining curve fit error. The human motion portion of the motion event signal may be detected by taking the value of a specific point on the curve (for example the center if the window) and comparing it to a predetermined threshold value. In some implementations, noise magnitude estimates and/or curve fit error errors may be estimated by the processor.

Implementations of the disclosed subject matter provide systems and methods that consider the shape of the motion event signal received from one or more sensors (e.g., that may include human movement, human walks, or the like, and that may include noise signals) in the time domain, and estimate the parameters (e.g., magnitude) of the corresponding modeled curves (e.g., a noise magnitude estimate, a curve fit error, and the like). The implementations of the disclosed subject matter produce an estimate of human motion from the motion event signal (e.g., a signal indicating human movement, such as a walk event, from the sensor), and provides an estimate of each modeled noise source, as well as the remaining fit error.

In traditional systems, a linear analog filter or a digital filter is used to suppress the noise of a signal detected by a sensor. Filters of present systems include complex linear filters such as Butterworth, Chebyshev, or Bessel filters. The filters of such traditional systems are designed in the frequency domain. In contrast, the filters of the implementations of the disclosed subject matter are designed in the time domain. The frequency domain filters of traditional system only produce a filtered signal, and do not indicate nor help determine the noise that was filtered out. That is, the systems and methods disclosed herein may provide an advantage in that the motion event signals from the one or more sensors may be obtained in the time domain, through testing and data acquisition, which simplifies the design of the filter. Another advantage may be that the motion event signal from the sensor may be more easily divided into a desired signal (e.g., the signal representing human motion, such as walking), one or more noise signals, and fit error. The systems and methods as disclosed throughout may provide nonlinear algorithms with increased simplicity and effectiveness, such as raising detection thresholds for a determined magnitude and time based on a priori knowledge of the detected type of noise, or clamping the estimated signal by the sensor to avoid overshoot.

The systems and methods of the disclosed subject matter provide noise suppression, which allows for the use of a low-cost and compact ambient motion sensor. Most present systems typically use larger sensors, as low-cost and compact ambient motion sensors typically have a less desirable signal-to-noise ratio.

Noise sources that may be identified and correlated for known events or sensor data may be used by systems and methods of the disclosed subject matter to dynamically adjust the ambient motion threshold (e.g., a detection threshold value). For example, noise sources may be identified in part, but may not be fully identifiable. Implementations of the disclosed subject matter may determine how much uncaptured noise can be expected, and what the shape of the noise (e.g., in a curve) may be as a function of time.

For example, electrostatic discharge may create noise in a motion event signal detected by a sensor. The electrostatic discharge may have a characteristic time signature that can be identified using the systems and methods of the disclosed subject matter. The extent to which the electrostatic discharge may be compensated for can be determined by testing. An upper bound as a function of time (e.g., an envelope) can be determined using the systems and methods of the disclosed subject matter. The upper bound may be selected so as to contain the noise. The sensor noise (including the effects of the electrostatic discharge) may be compensated for by filtering the noise from the motion event signal (e.g., subtracting the known noise). To the extent that the sensor noise (including the effects of the electrostatic discharge) may not be compensated for by filtering at least a portion of the noise from the motion event signal, the systems and methods of the disclosed subject matter may raise the human motion (e.g., human walk) detection threshold to avoid false positives.

Jarring of the sensor may create noise in a motion event signal detected by sensors. The jarring may be correlated to accelerometer sensor data. By monitoring for jarring using a secondary sensor, jarring may be detected, and the magnitude of the jarring may be estimated. A suitable envelope may be selected by the systems of the disclosed subject matter to increase the detection threshold value.

Internal radio transmissions may also create noise signals which may affect the motion event signals detected by sensors. Since the software running on a sensor (e.g., an ambient motion detection device) initiates radio transmissions, it can also initiate raising the ambient motion (e.g., human movement, human walk, or the like) detection threshold value using a suitable envelope that may be selected by the systems of the disclosed subject matter.

The total amount to which a detection threshold value may be raised can be determined by the sum of the individually identified noise signals of the motion event signal (e.g., the noise from electrostatic discharge, jarring, internal radio transmissions, and the like). In implementations of the disclosed subject matter, the detection threshold value may be raised so as to avoid false positives in the attempt to detect human motion, rather than trying to filter all noise from the sensor signal.

Implementations of the disclosed subject matter may reduce false negatives of typical sensor motion detection systems by compensating for one or more noise types so as to determine whether there is a human motion event in the motion event signal. Such implementations may provide for the use of low-cost and compact ambient motion sensors, in comparison to the larger, more expensive sensors with an increased signal-to-noise ratio that are typically used in present systems. Implementations of the disclosed subject matter may be used for sensors for home security or other proximity detection applications.

That is, in the implementations discussed below in connection with FIGS. 1-11, sensor-based motion detection (e.g., passive infrared (PIR) ambient motion detection or the like) may be used to detect human motion. Sensor-based motion detection systems and methods are provided that may separate signals representing human motion (e.g., human walking) detected by a sensor from noise and/or disturbances. Sources of noise and/or disturbances may include high frequency sources, such as 6lowpan Tx-coex (noise from devices transmitting signals using Internet Protocol (IPv6) and Low-power Wireless Personal Area Networks (LoWPAN)), electrostatic discharge (ESD), and/or noise from an HVAC system in a home or building (heating, ventilation, and air conditioning). The noise and/or disturbances from HVAC may have a broader spectrum than other sources, and may induce high frequencies (e.g., high frequency noise). Sources of noise and/or disturbances may induce low frequency noise in a sensor of a device, such as EMI (electromagnetic interference) from radio transmissions, emissions from light emitting diodes (LEDs), pets, or the like.

FIG. 1 shows a method 100 of detecting human movement with a sensor of a device, such as in a smart-home environment discussed in connection with FIGS. 8A-8B, according to implementations of the disclosed subject matter. The sensor of the device may be one or more of sensors 71, 72 shown in FIGS. 2B, 8A, 8B, and 10, and described below. The sensors 71, 72 may include one or more of a passive infrared sensor (PIR), an accelerometer, and/or any type of motion sensor as described below. The sensors 71, 72 may be part of a device that detects human motion and may include, for example, a processor 200 as shown in FIG. 2B and described below.

At operation 110 shown in FIG. 1, a motion event signal in response to movement detected by the sensor (e.g., one of sensors 71, 72) may be generated. A parameterized curve may be generated, at a processor (e.g., processor 200 shown in FIGS. 2A-2B) coupled to the sensors 71, 72, to represent the detected motion at the sensors 71, 72 based on the motion event signal at operation 120. The processor may be part of the device that detects human motion. An example parameterized curve is shown in FIG. 2D. In some implementations of the disclosed subject matter, the parameterized curve may be generated at operation 120 using at least one of low-order polynomials, a sum of sinusoids over a predetermined frequency range, and as steps or spikes.

The parameterized curve may be fitted, at the processor 200, to a predetermined window of sensor data captured by the sensors 71, 72 that includes at least a portion of the motion event signal to filter the motion event signal at operation 130 shown in FIG. 1. In the example parameterized curve shown in FIG. 2D, the window of sensor data may include portions of time before and/or after the point $t_k$. In some implementations of the disclosed subject matter, the parameterized curve may be defined for the predetermined window of the sensor data. In some implementations, the processor 200 may fit the parameterized curve to the predetermined window using a least-squares optimization.

The processor 200 may determine which portions of the motion event signal detected by sensors 71, 72 may be part of a noise signal and/or a human motion signal, as well as remaining curve fit error. As described in detail below, the processor 200 may form a fitted human motion signal and a fitted noise signal, and may determine a remaining curve fit error. In some implementations, the fitted human motion signal, the fitted noise signal, and the remaining curve fit error may be determined at the processor 200 by curve shapes in a time domain.

At operation 135 as shown in FIG. 1, the processor 200 may determine a noise source signal magnitude estimate of a known noise based on the fitted parameterized curve to the predetermined window. The processor 200 may determine that a portion of the fitted parameterized curve includes a noise source signal of a known noise, such as ESD, HVAC, EMI, RF, and the like. The processor 200 may determine a magnitude estimate of the known noise. A noise magnitude estimate (e.g., a noise source signal magnitude estimate) may be an estimate of the amount and/or magnitude of noise in the motion event signal by the curve fit filter 210. In some implementations, different noise magnitude estimates may be made for different types of noise (e.g., noise from ESD, HVAC, EMI, RF, and the like).

At operation 140 as shown in FIG. 1, a curve fit error may be determined, at the processor 200, based on the fitted parameterized curve to the predetermined window. A curve fit error may be determined, by the processor 200, of an amount and/or magnitude of error in fitting the parameterized curve to the predetermined window.

At operation 145, the processor 200 may determine a detection threshold value based on the curve fit error, the noise source signal estimate of the known noise, and zero or more noise magnitudes estimated at the processor 200 from other sources. The detection threshold value may be dynamically changed over time (e.g., based on changes to the noise magnitude estimate and/or the curve fit error and past values of the detection threshold). An estimated true motion event signal may be determined to correlate with human motion by the processor 200 based on a comparison between a value of a point on the parameterized curve and a detection threshold value at operation 150. In some implementations, the processor 200 selects the value of the point on the parameterized curve to be within the predetermined window, such as in the middle of the predetermined window. For example, the processor 200 may select the value at the point along the curve at point $t_k$, as shown in FIG. 2D. The estimated true motion event signal may be determined by processor 200 by filtering the motion event signal by subtracting the noise magnitude estimate so as to compensate for sensor noise. The processor 200 may adjust the detection threshold value based on the noise source signal magnitude estimate. In some implementations, the processor 200 may raise the detection threshold value when a noise magnitude estimate is based on notifications of internal radio transmissions of a device that may include the sensor.

Figure 3A:
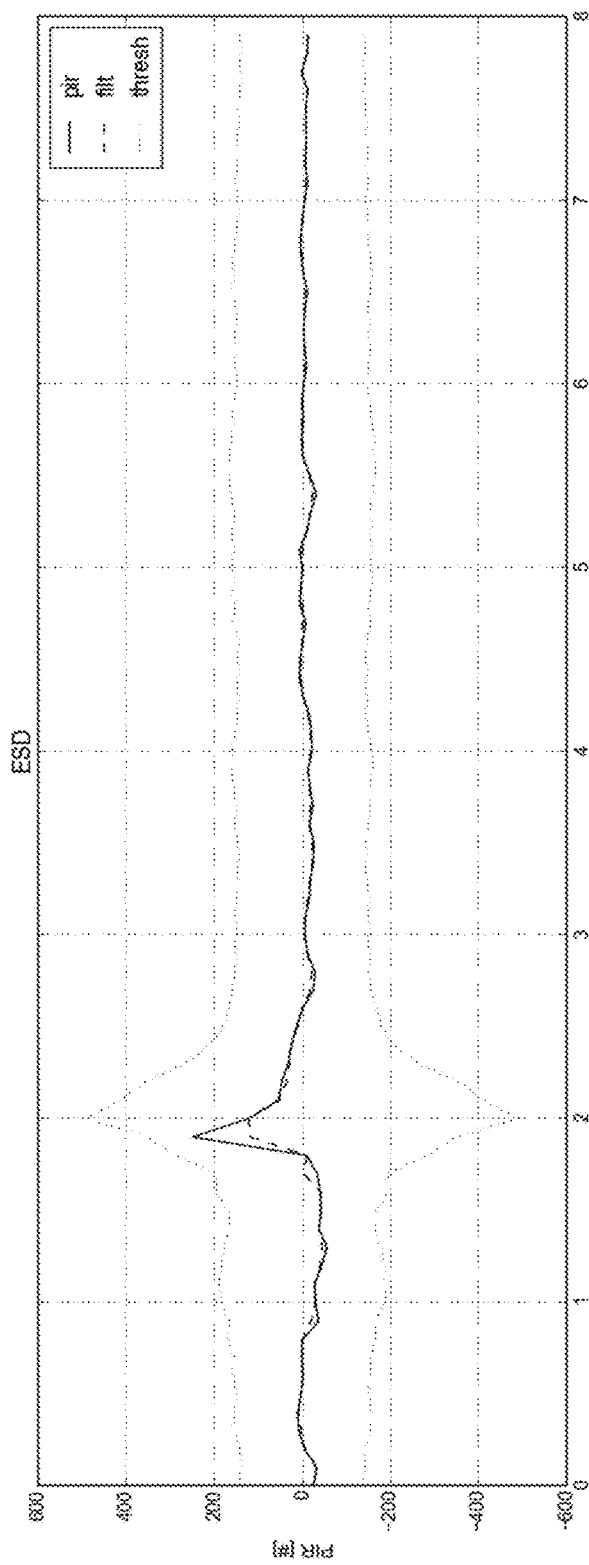
FIGS. 3A-3B show a raw input signal to a sensor and a filtered input signal using the processor FIG. 2A for electrostatic discharge (ESD) noise according to an implementation of the disclosed subject matter.
Figure 3B:
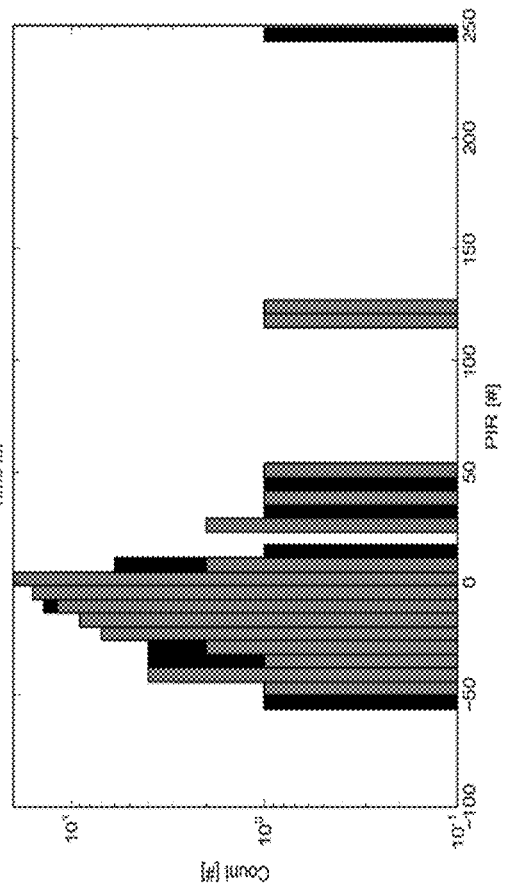
Figure 4A:
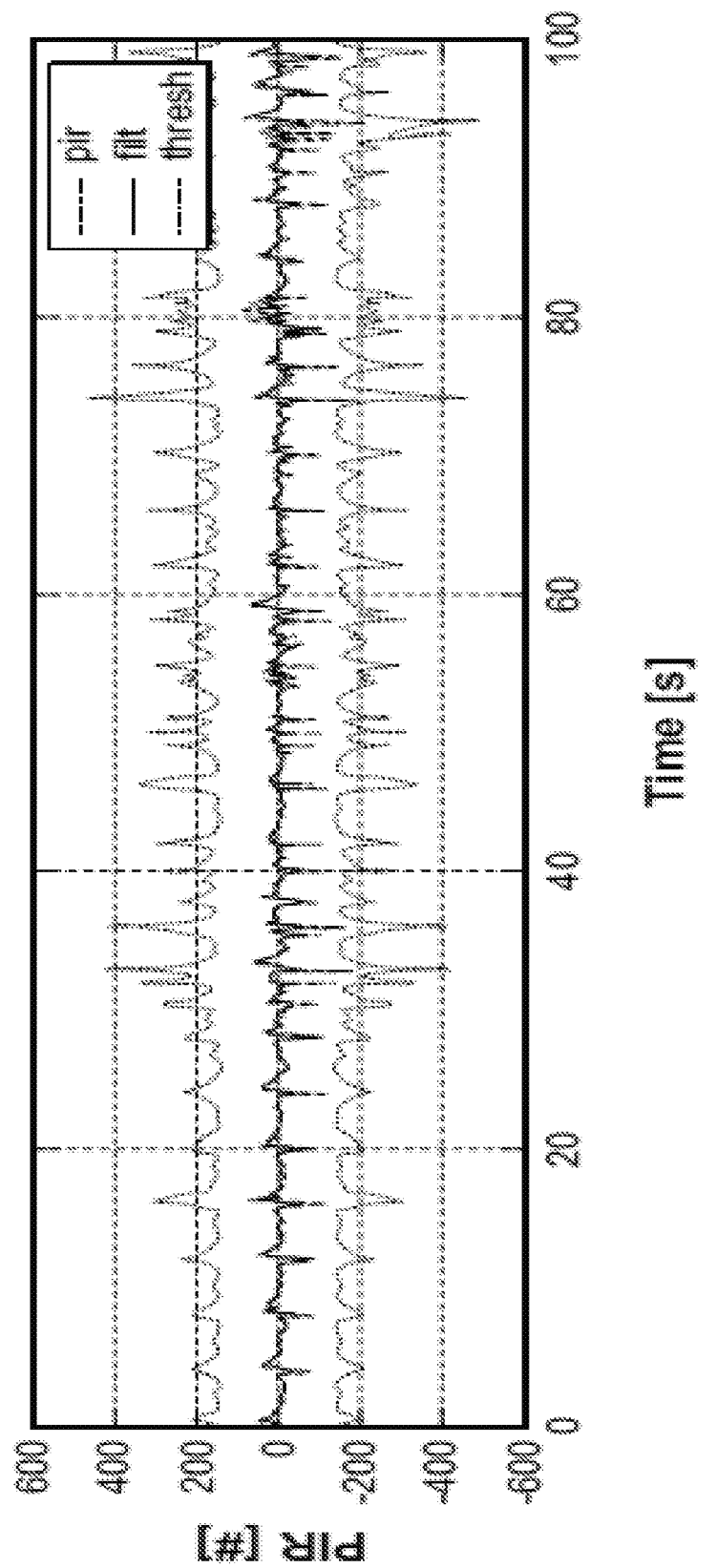
FIGS. 4A-4B show a raw input signal to a sensor and a filtered input signal using the processor of FIG. 2A for 6lowpan Tx-coex noise (noise from transmission of Internet Protocol (IPv6) over Low-power Wireless Personal Area Networks) according to an implementation of the disclosed subject matter.
Figure 4B:
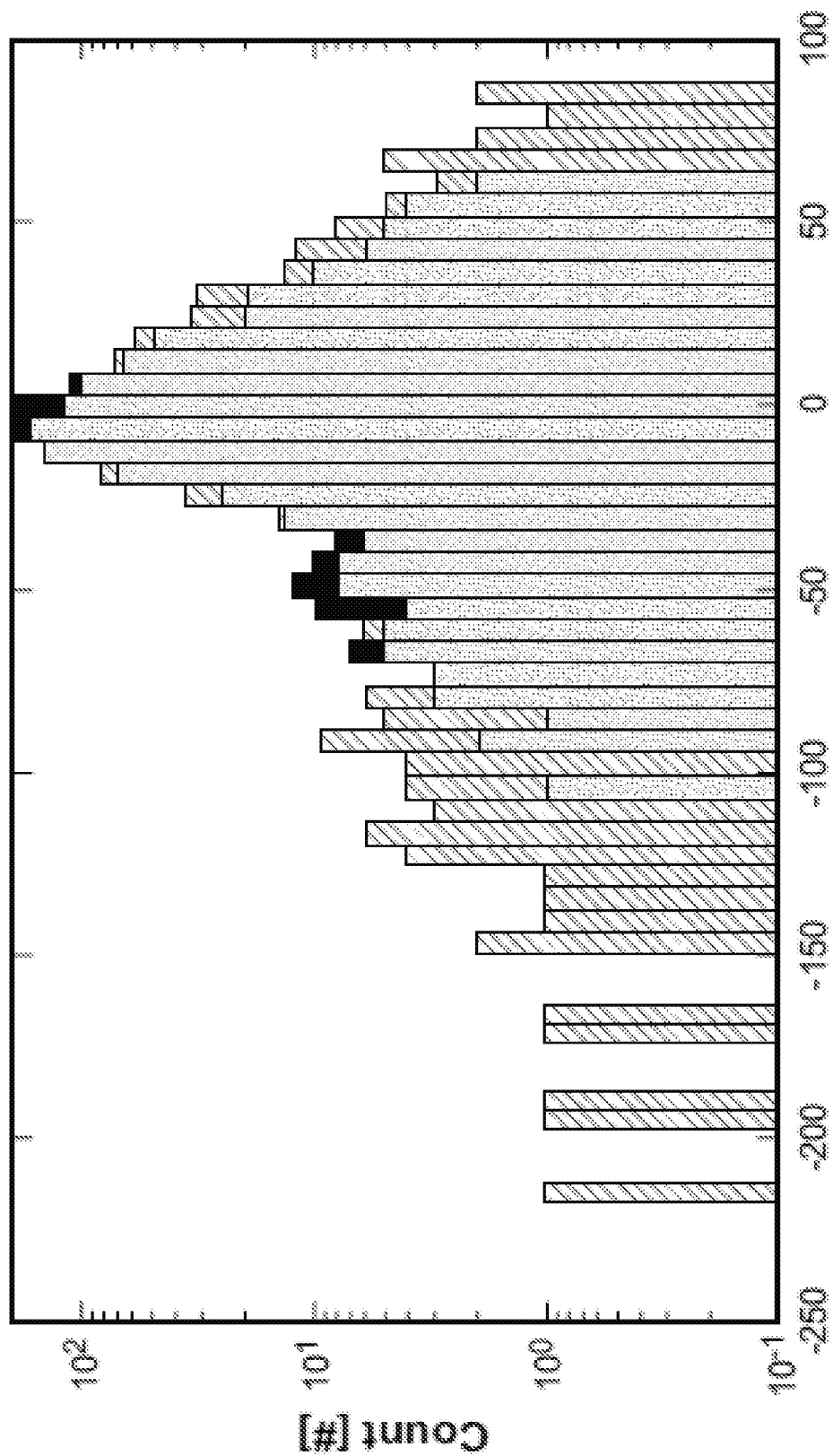
Figure 5A:
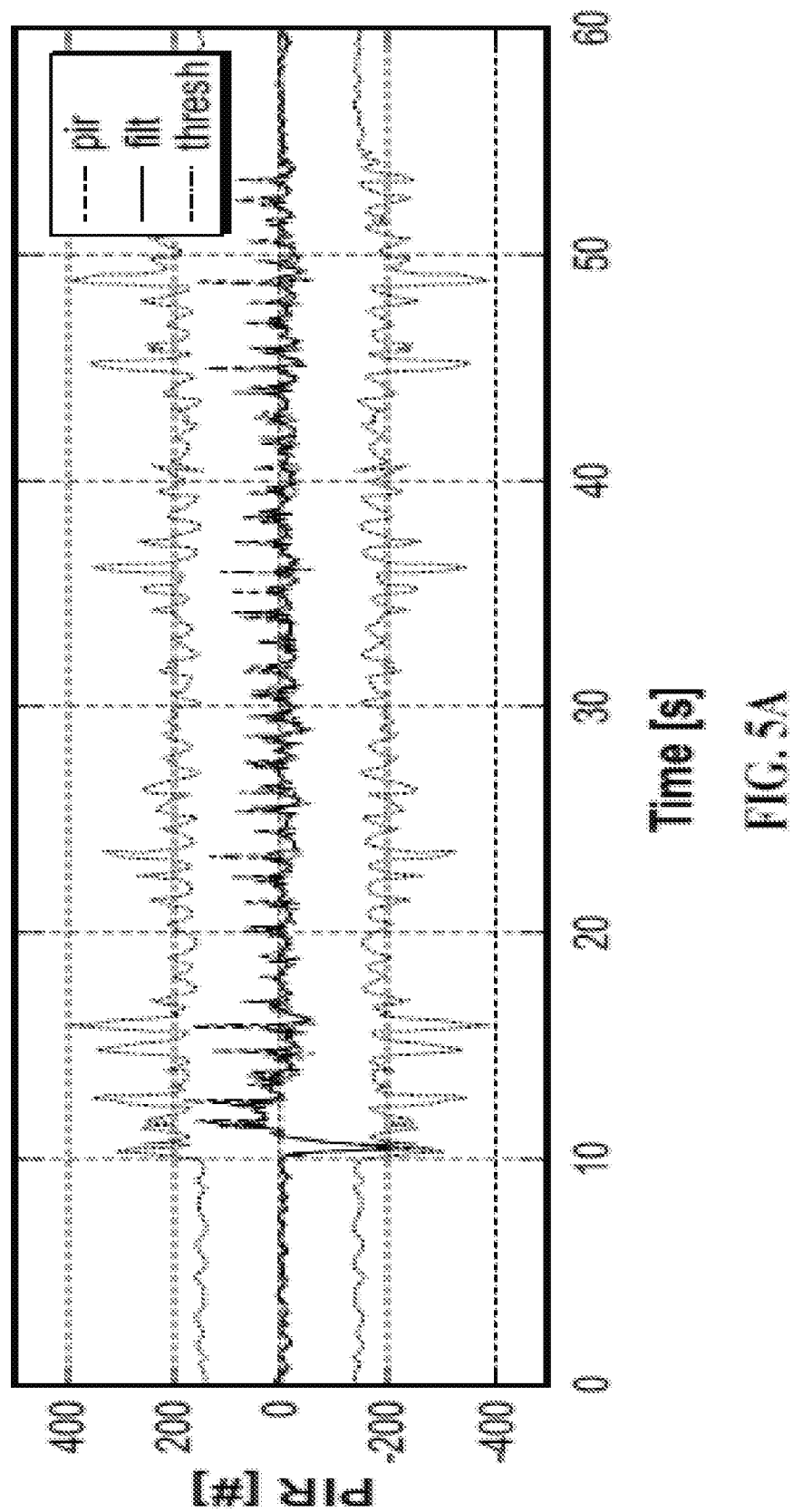
FIGS. 5A-5B show a raw input signal to a sensor and a filtered input signal using the processor of FIG. 2A for jarring noise according to an implementation of the disclosed subject matter.
Figure 5B:
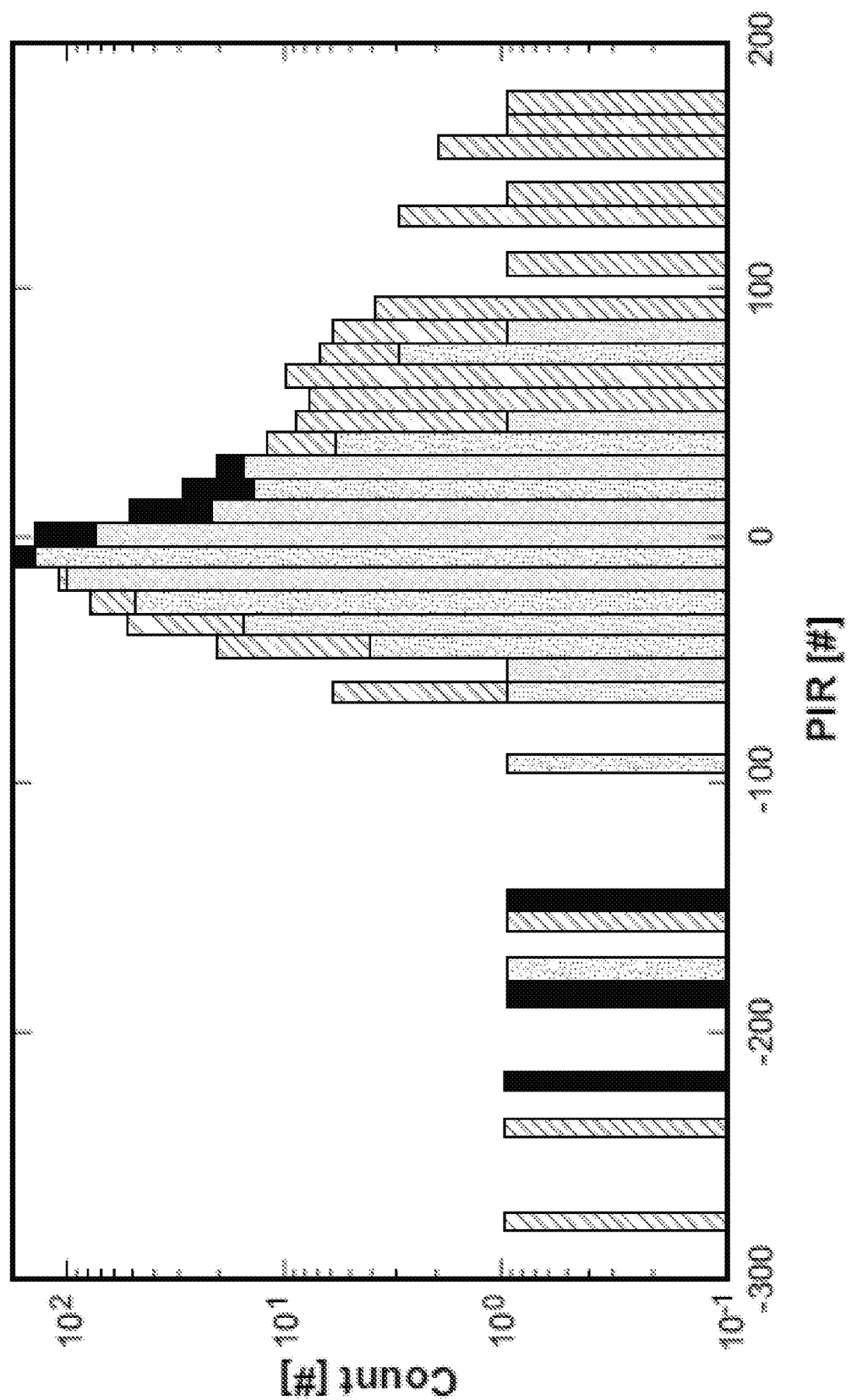

In some implementations of the method 100 of FIG. 1, the detection threshold value may be raised by the processor 200 for a determined magnitude and time based on one or more types of noise of the noise magnitude estimate, as discussed in detail below in connection with FIGS. 3A-7B. That is, the detection threshold value may be continually adjusted over time for ESD noise as shown in FIG. 3A, based on the magnitude of a portion of the motion event signal (e.g., a noise signal component) detected by the sensor and/or noise magnitude estimate. Similarly, the detection threshold value may be continually adjusted over time for 6lowpan Tx-coex noise as shown in FIG. 4A, and may be continually adjusted over time for jarring as shown in FIG. 5A.

In some implementations of method 100, the processor 200 may estimate a noise signal shape that may be a portion of the motion event signal (e.g., the noise magnitude estimate) as a function of time to be expected when the noise signal is partially identified. The processor 200 may determine an upper bound of the noise magnitude estimate as a function of time. The upper bound may include a noise signal, which may be a portion for the motion event signal. The processor 200 may determine that the noise may correspond to an electrostatic discharge signal detected by the sensors 71, 72. In some implementations, the processor 200 may clamp a motion signal estimate (e.g., an estimated true motion event signal) by the motion event signal detected by the sensors 71, 72 to avoid overshoot and minimize errors in determining the motion signal estimate.

In some implementations, the processor 200 may correlate the noise magnitude estimate (e.g., the noise source signal magnitude estimate of a known noise, the noise magnitudes estimated from other sources, or the like) with a second data signal from a second sensor. For example, the motion event signal may be primarily detected by sensor 71, and sensor 72 may be the second sensor used to correlate the noise magnitude estimate and/or a noise portion of the motion event signal detected by sensor 71. The processor 200 may determine the noise magnitude estimate, and generate an envelope to increase the detection threshold value. The processor 200 may correlate the noise magnitude estimate and/or a noise portion of the motion event signal with jarring of the sensor based on accelerometer data from the second sensor (e.g., sensor 72).

Figure 2A:
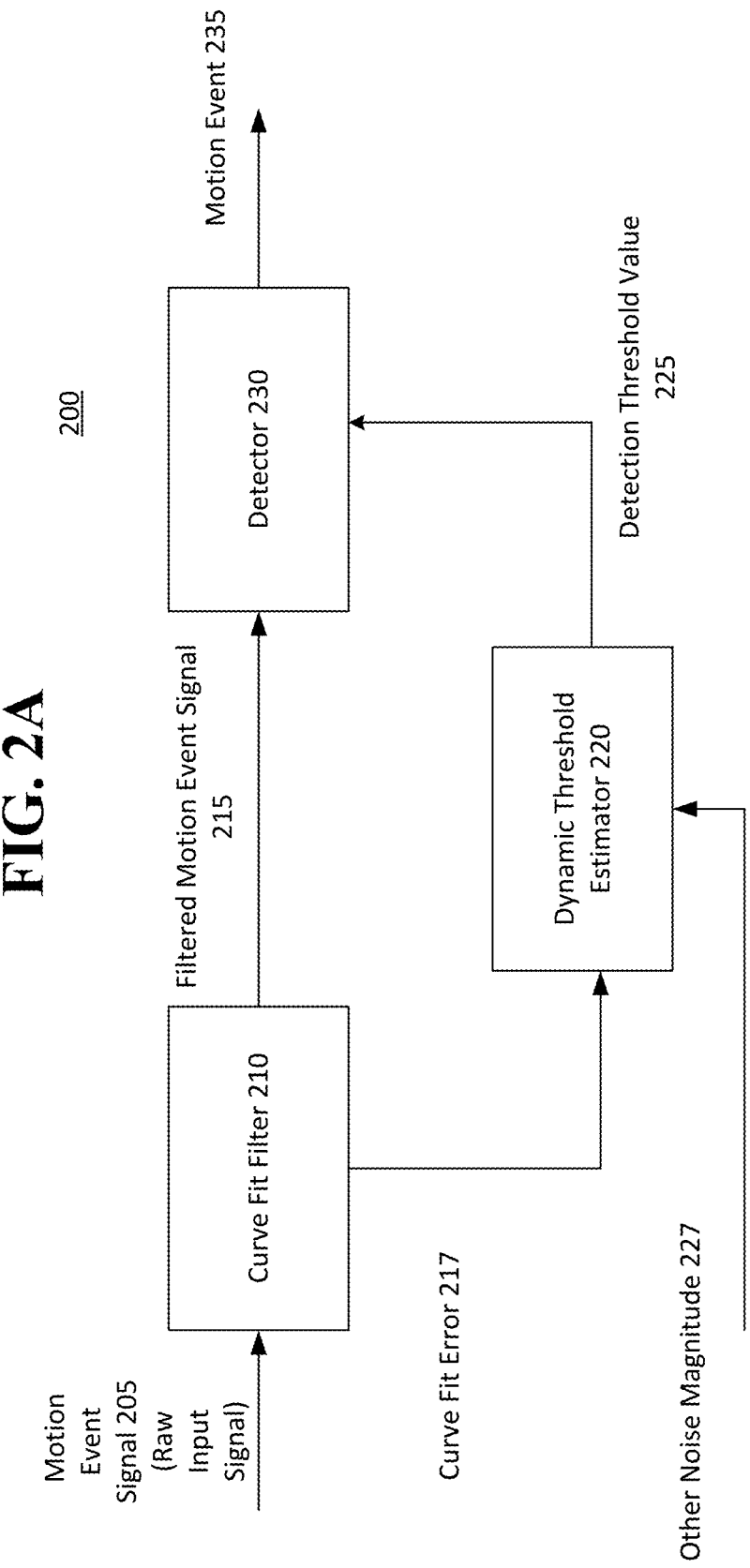
FIG. 2A shows a curve fitter, a dynamic threshold estimator, and a detector of a processor according to an implementation of the disclosed subject matter.
Figure 2B:
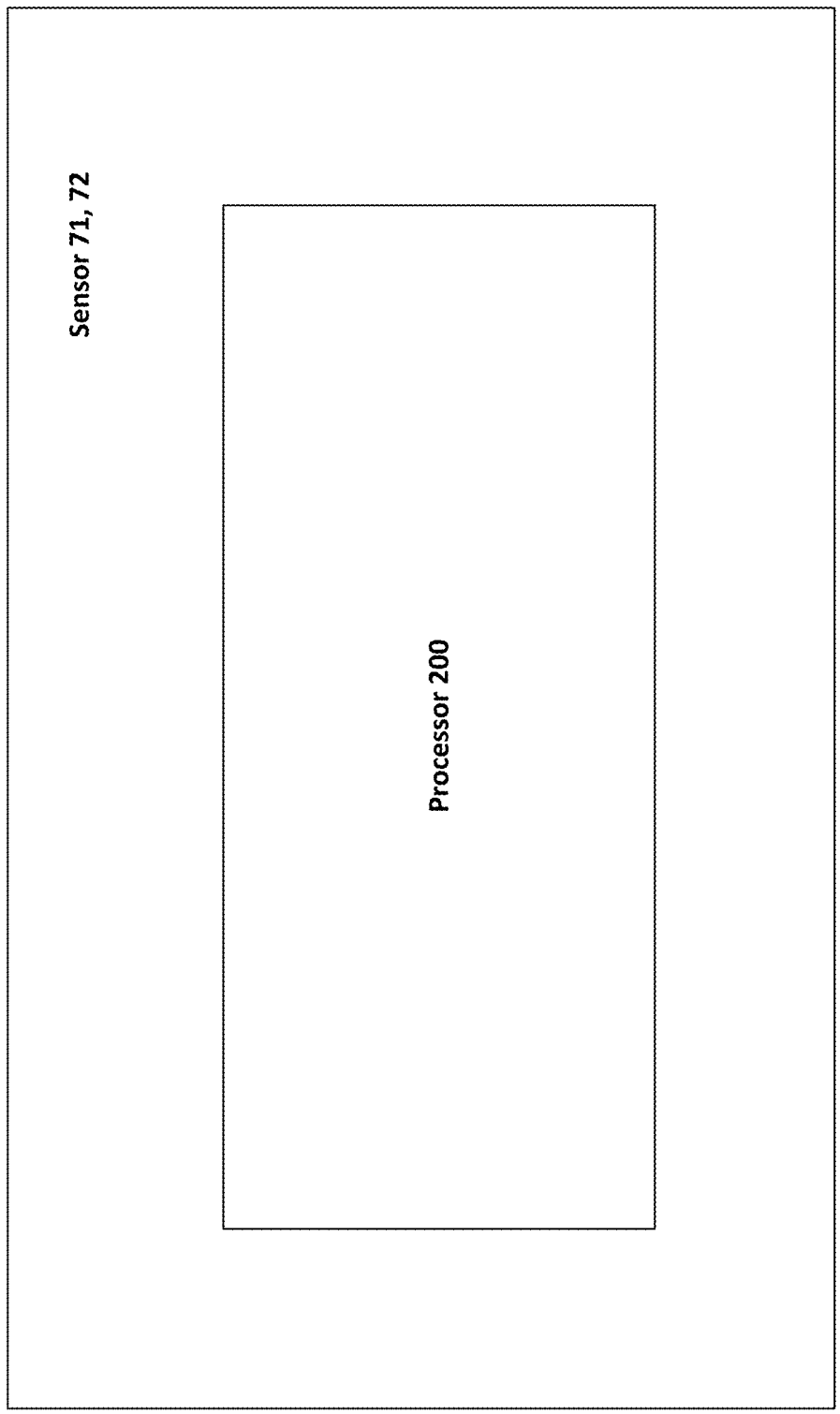
FIG. 2B shows an example sensor including the processor of FIG. 2A according to an implementation of the disclosed subject matter.

FIG. 2A shows the processor 200 that includes curve fit filter 210, a dynamic threshold estimator 220, and a detector 230 according to an implementation of the disclosed subject matter. As shown in FIG. 2A, the processor 200 may include a curve fit filter 210 to receive an input signal (e.g., a motion event signal 205) from a sensors 71, 72. The curve fit filter 210 may output a filtered motion event signal 215 based on the received motion event signal 205 (e.g., raw input signal), and may determine a curve fit error, which may be output as curve fit error 217), as discussed above. The dynamic threshold estimator 220 may determine and output a detection threshold value 225 based on the estimated fit error magnitude (e.g., curve fit error 217) from the curve fit filter 210 and based on one or more noise magnitude 227 (e.g., a noise source signal magnitude estimate of a known noise and/or noise magnitude estimates from other sources, as discussed above. The detector 230 may output a determined motion event 235 (e.g., an estimated true motion event signal) based on the filtered signal 215 from the curve fit filter 210 and a detection threshold value 225 from the dynamic threshold estimator 220. FIG. 2B shows that the processor 200 of FIG. 2A may be integrated with and/or communicatively coupled to the sensors 71, 72 as part of a device to sense human movement. These sensors 71, 72 may be part of a security system shown in FIGS. 8A-8B and discussed in detail below.

The filtering (e.g., low pass filtering) may be performed by the curve fit filter 210 of the processor 200, where $$z(k)=f(y(k-n), \ldots, y(k+n)),$$

where z) is the curve fitter output, k is an index to samples (e.g., time instances) captured by the sensors 71, 72, f is a curve fit function, and y is a measurement from before a particular point (k−n) to after a particular point (k+n). Filtering, such as performed by the curve fit filter 210, may be non-causal if a time delay is introduced. This may simplify the design of the curve fit filter 210, as a predictor may not be needed. In some implementations of the disclosed subject matter, a least squares fit may be performed by the curve fit filter 210 for each sample k, where:

$$z(k)=p(0)+p(1)k+ \ldots p(m)k^n,$$

where p is a coefficient for the polynomial, and m is the polynomial order of fit, and where the following may provide a least-squares fit:

$$p=\arg\min p\Sigma i=[-n, \ldots ,+n]|z(k+i)-y(k+i)|^2$$

The above may find the coefficients of the polynomial, and minimize fitting error. The following equations may be used to implement the curve fit filter 210:

$$Z=[z(k-n); \ldots ;z(k+n)], Y=[y(k-n); \ldots ;y(k+n)]$$

where Z is the vector of curve fitted points, Y is the vector of the set of measurements, such that $$Z=Xp,$$

Where Xp is the matrix X multiplied by the parameter vector p, $$X=[1,(-n),(-n)^2, \ldots ,(-n)^m; \ldots ;1,(n),(n)^2,(n)^m]$$

where m is the polynomial order of fit, and X depends on n and m. Using X and Y, the least-squares fit can be reformulated as $$p=\arg\min_p \|Xp-Y\|,$$

and where p is the vector or coefficients of the polynomial. The solution to the above may be expressed as a pseudo-inverse (e.g., in matrix format):

$$p=(X^TX)^{-1}X^TY=QY, Q=(X^TX)^{-1}X^T$$

where yhat(k)=z(k)=p0=$Q_1 \cdot Y$=aY, and $Q_1$ is the first row of Q. The implementation disclosed above for the curve fit filter 210 may be similar to a moving average filter, which may be linear and constant.

In the equations above, n may be selected, and the window length may be 2n+1, which may be representative of the "noisiness" of a measured signal from the sensors 71, 72. The variable m may be selected for a polynomial order of fit, which may be representative of the "curviness" of a signal. With these selections, Q may be determined, and $Q_1$ may be retained.

The dynamic threshold estimator 220 may use fitting error (e.g., error by the curve fit filter 210, such as the curve fit error 217) as a measure of noise, which can be used to adjust a threshold (e.g., detection threshold value 225). FIG. 3A shows raw data from a passive infrared (PIR) sensor (labeled as "pir" in FIG. 3A; the PIR sensor may be sensors 71, 72), as well as filtered (labeled as "filt" in FIG. 3A) data which has been filtered by the curve fit filter 210, and the detection threshold values (labeled as "thresh" in FIG. 3A) that are adjusted and/or change. FIG. 3A shows the raw PIR signal filtered for ESD noise, and the dynamic change of detection threshold values over time. FIG. 3B shows the raw and filtered PIR signal in terms of count value. FIG. 4A shows the raw PIR signal filtered for 6lowpan Tx-coex noise, and the dynamic change of detection threshold values over time. FIG. 4B shows the raw and filtered PIR signal in terms of count value. FIG. 5A shows the raw PIR signal filtered for noise from jarring (e.g., of the PIR sensor, which may be sensors 71, 72), and the dynamic change of threshold values over time, the raw and filtered PIR signal in terms of count value. FIG. 5C shows the raw and filtered PIR signal in terms of count value.

Figure 6A:
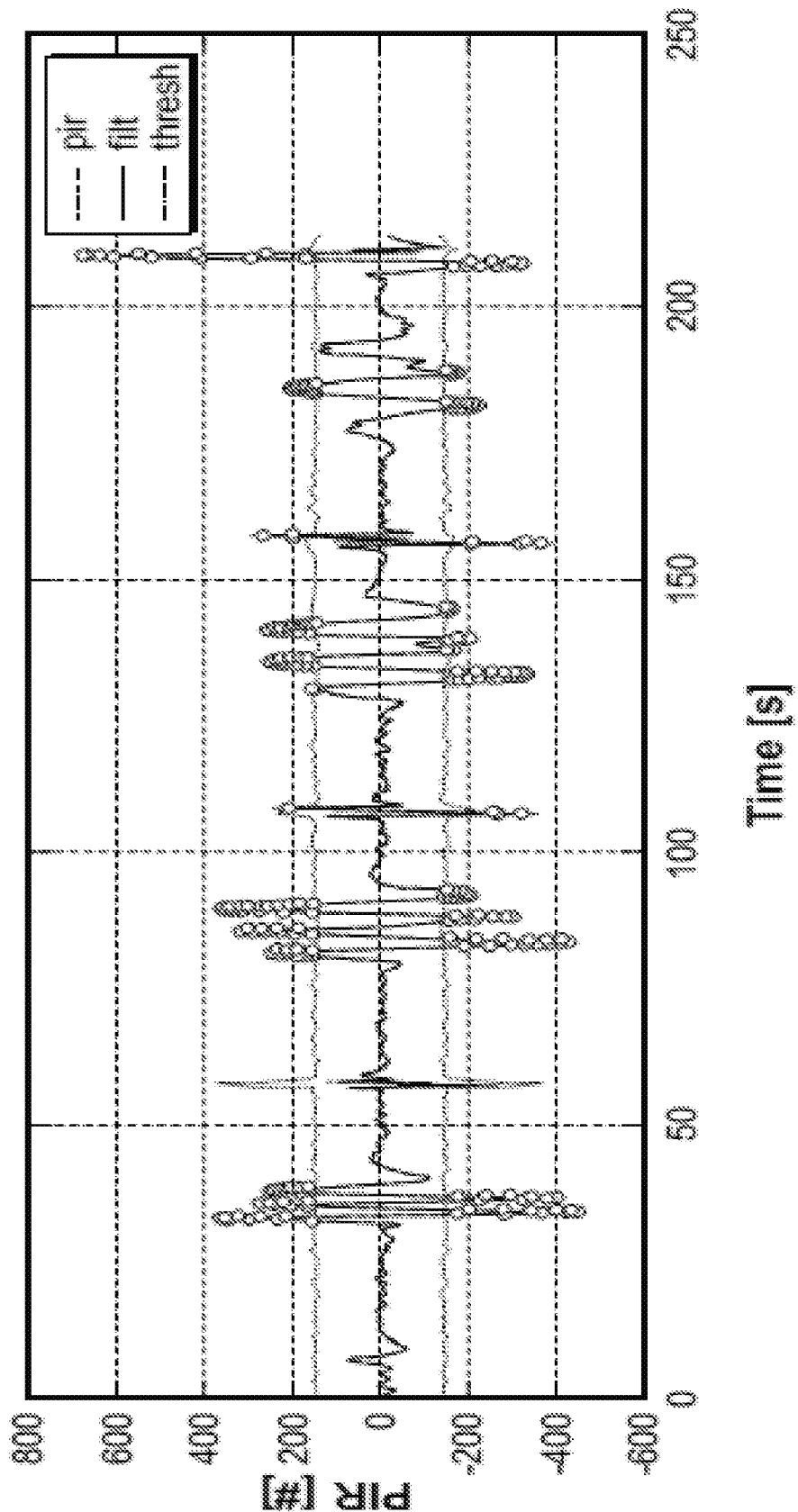
FIGS. 6A-6B show a raw input signal to a sensor and a filtered input signal using the processor of FIG. 2A for a normal human walk pattern according to an implementation of the disclosed subject matter.
Figure 6B:
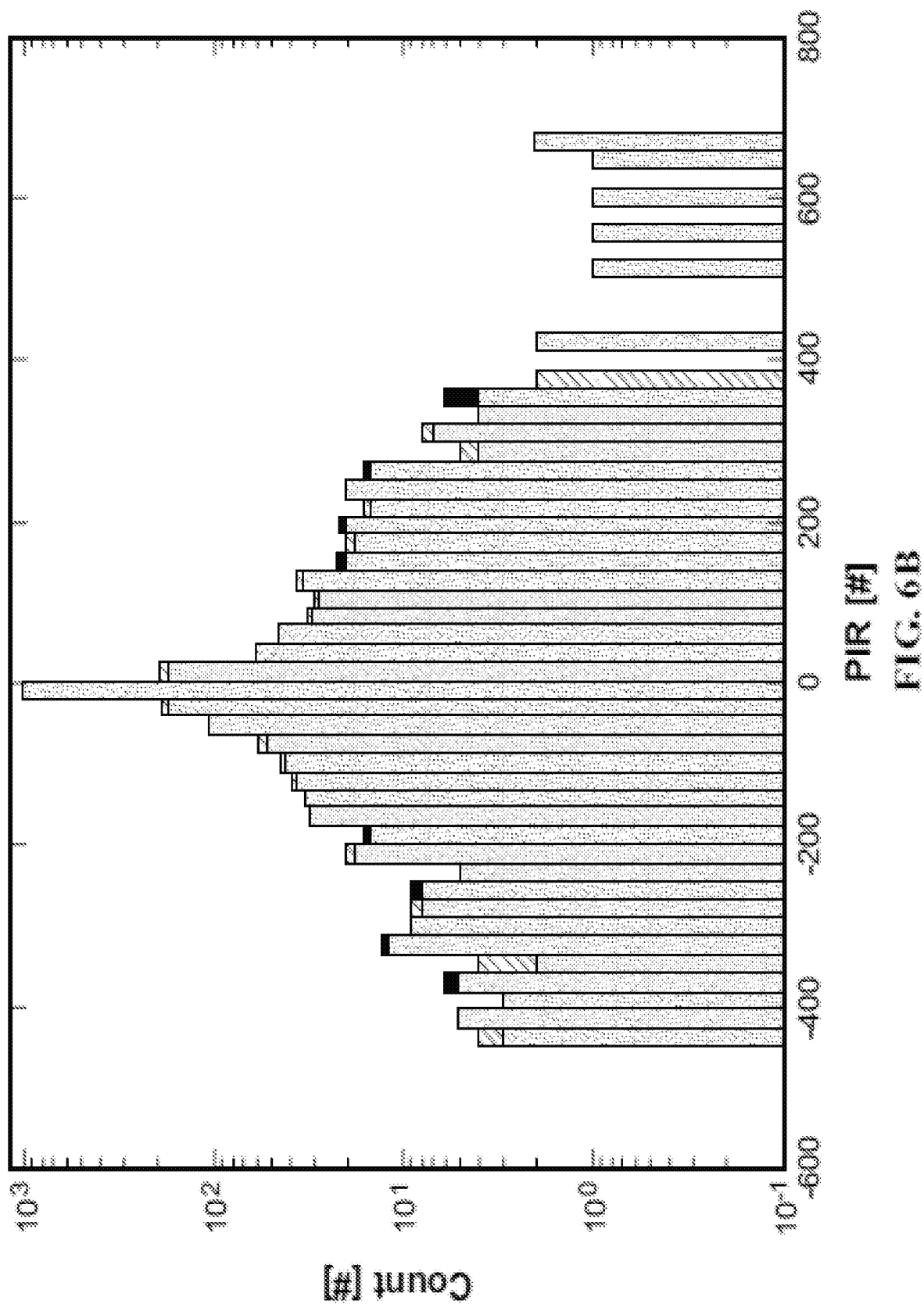
Figure 7A:
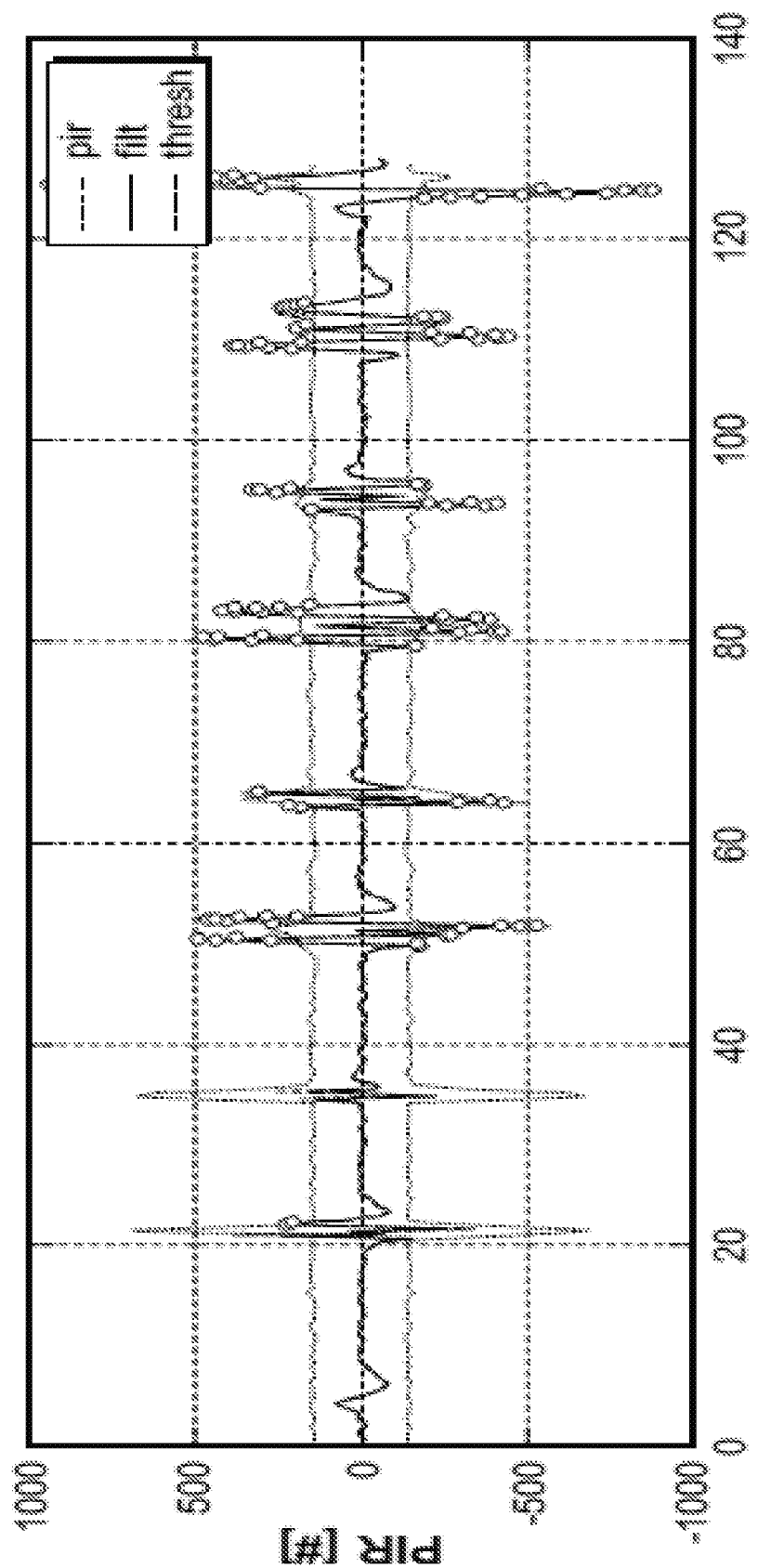
FIGS. 7A-7B show a raw input signal to a sensor and a filtered input signal using the processor of FIG. 2A for a fast human walk pattern according to an implementation of the disclosed subject matter.
Figure 7B:
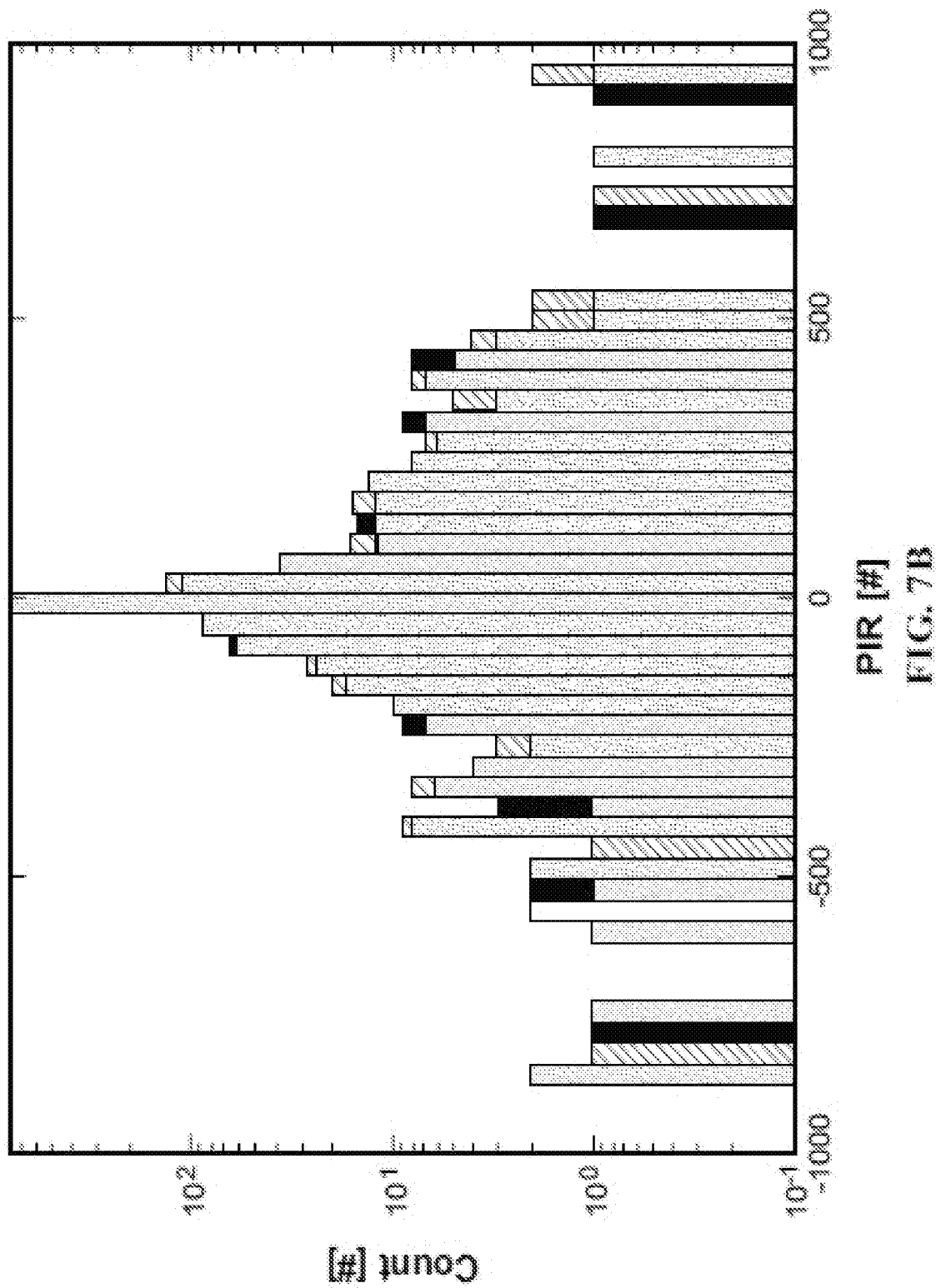

FIGS. 6A-6B show that the dynamic threshold estimator 220 may be used to adjust a detection threshold value for the filtered and unfiltered PIR signals (e.g., motion event signal 205 and filtered motion event signal 215) that detect a normal human walk signal that is detected by the PIR sensor (e.g., sensors 71, 72). FIGS. 7A-7B show that the dynamic threshold estimator 220 may be used to adjust a threshold for the filtered and unfiltered PIR signals that detect a fast human walk signal.

The curve fit filter 210, the dynamic threshold estimator 220, and the detector 230 of a processor 200 shown in FIG. 2A may be used to estimate the noise level (e.g., so as to adjust a threshold value and to determine a motion event, such as a human walk). For example, a fitting error (e.g., the curve fit error 217) may be determined, and used to estimate the noise level. In some implementations, a fitting derivative error (e.g., the changes to the fitting error over time) may additionally be used to estimate the noise level. When estimating noise, a "forgetting factor" may be applied when the noise level dissipates, so that the detection threshold value 225 can be adjusted. That is, the detection threshold value 225 may be adjusted based on the determined fitting error (e.g., the curve fit error 217). The processor 200 may determine that the motion signal estimate (e.g., an estimated true motion event signal) is not larger than the raw PIR signal (which may act as a "clamp"). The processor 200 may lower and/or change the detection threshold value 225 based on the estimated noise level to gain field of view (FOV). This may be used to determine whether there is a motion event, such as a human walk, in the signal detected by the PIR sensor (e.g., sensors 71, 72).

The above-described curve fitting and noise estimation in connection with FIG. 2A may have increased effectiveness with signals having sharp peaks, such as those for ESD noise (e.g., as shown in FIGS. 3A-3B) and Tx-coex noise (e.g., as shown in FIGS. 4A-4B). The fit-error based threshold which is raised by the processor 200 may increase the ability to detect motion event (e.g. human walking) using a PIR sensor (e.g., sensors 71, 72). The fit-error based thresholding may address noise from a plurality of sources that may be compounded (e.g., combined HVAC noise and Tx-coex noise). In implementations of the disclosed subject matter, raising a threshold may not necessarily lead to false negatives (e.g., in terms of detecting human movement), as a walk signal of the signal detected by the sensors 71, 72 may add to the overall signal detected by the sensors 71, 72. The dynamic adjustment of the detection threshold value 225 avoids disabling the sensor (such as done in prior systems) when high levels of noise are detected.

Figure 2C:
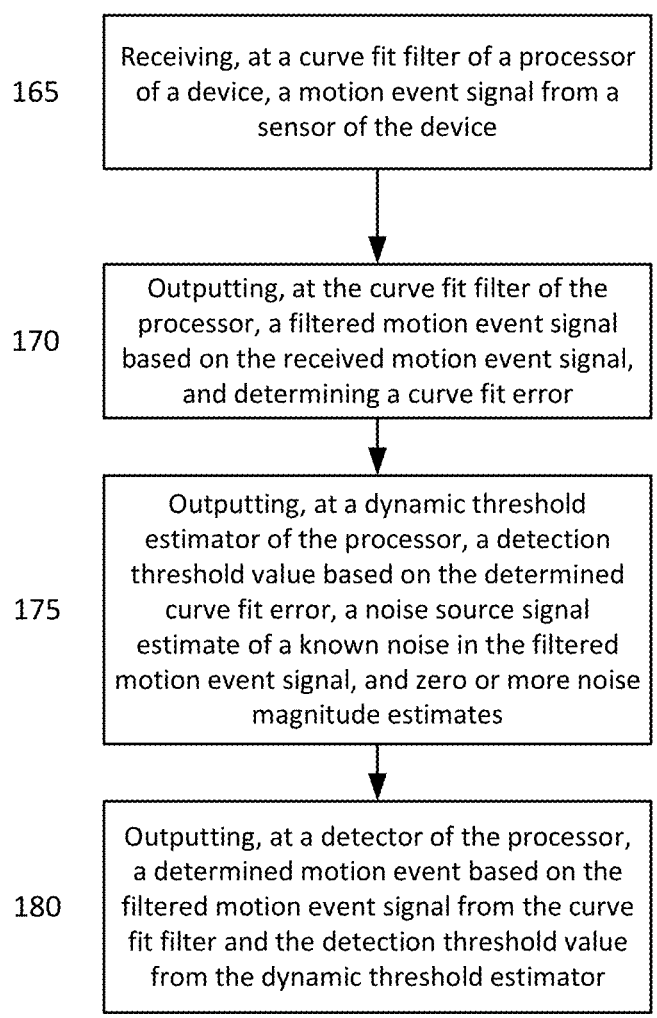
FIG. 2C shows another method of detecting human movement with a sensor of a device according to an implementation of the disclosed subject matter.
Figure 2D:
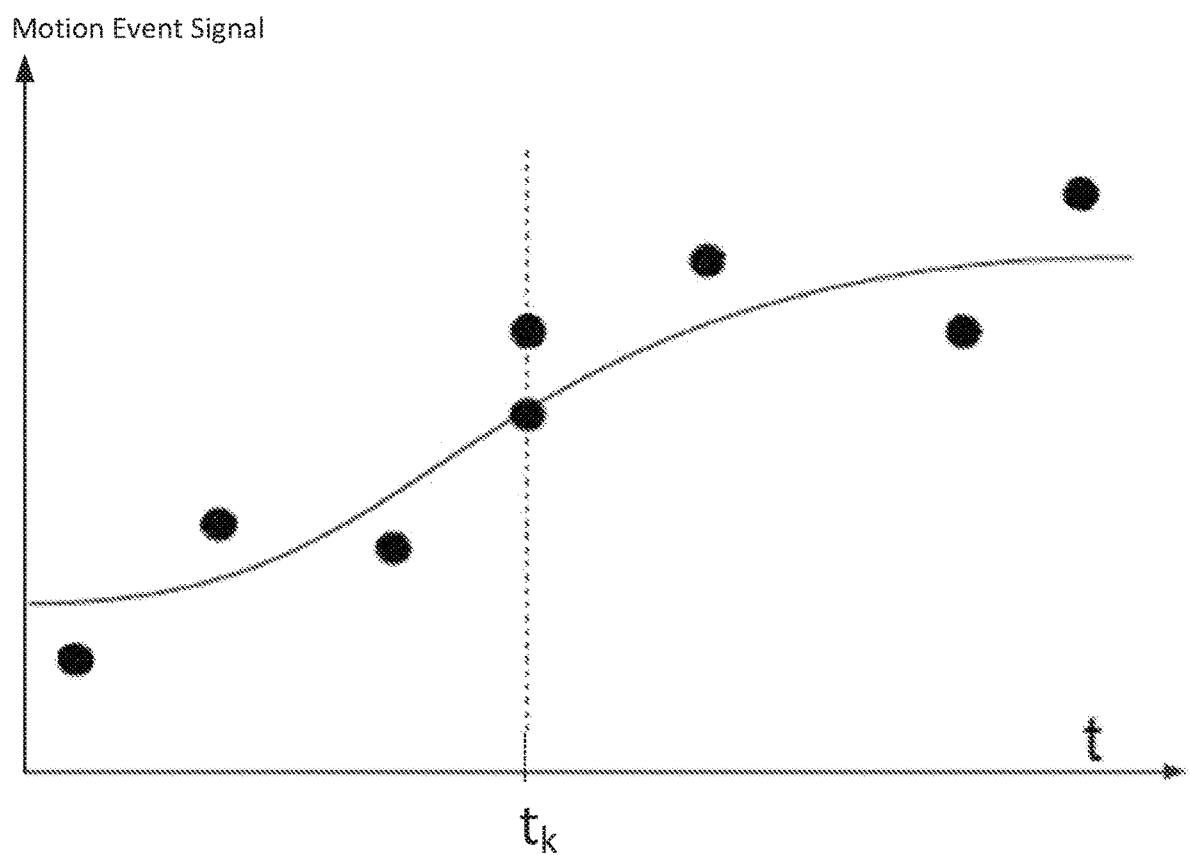
FIG. 2D shows a parameterized curve according to an implementation of the disclosed subject matter.

FIG. 2C shows a method of detecting human movement with a sensor according to an implementation of the disclosed subject matter. The method 160 may include receiving, at a curve fit filter 210 of the processor 200, a motion event signal 205 from a sensors 71, 72 at operation 165. The curve fit filter 210 may output a filtered motion event signal 215 based on the received motion event signal 205, and may determine a curve fit error (e.g., curve fit error 217) at operation 170. A dynamic threshold estimator 220 may output a detection threshold value 225 based on the determined curve fit error 217, a noise source signal estimate of a known noise in the filtered motion event signal 215, and zero or more noise magnitude estimates 227 at operation 175. A detector 230 may output a determined motion event 235 based on the filtered motion event signal 215 from the curve fit filter 210 and the detection threshold value 225 from the dynamic threshold estimator 220.

That is, FIGS. 2A-D show a system, including a processor 200, to detect human movement with a sensor (e.g., sensors 71, 72 shown in FIGS. 2B, 8A, 8B, and 10, and described below) according to implementations of the disclosed subject matter. The system may generate a motion event signal in response to movement detected by the sensors 71, 72. The processor 200 may be integrated with and/or communicatively coupled to the sensors 71, 72 (see, e.g., FIG. 2B). In some implementations, a device to detect human movement may include the processor 200, the sensors 71, 72, and a communications interface so that the device may communicate with, for example, the controller 73, the remote system 74, and/or the alarm device 76 via the network 70 as shown in FIG. 8B and described below.

As discussed throughout, the processor 200 may generate a parameterized curve (see, e.g., FIG. 2D) to represent the detected motion at the sensor (e.g., the motion event signal 205). The processor 200 may fit the parameterized curve to a predetermined window of sensor data captured by the sensor that includes at least a portion of the motion event signal. The processor 200 may determine a human motion event, as well as noise signals and curve fit errors based on the fitted parameterized curve to the predetermined window. The processor 200 may determine human motion based on a comparison between a value of a point on the parameterized curve and a detection threshold value.

The processor 200 may generate the parameterized curve using at least one of low-order polynomials, a sum of sinusoids over a predetermined frequency range, and as steps of spikes. In some implementations, the processor 200 may fit the parameterized curve to the predetermined window of the sensor data using parameter optimization. The parameter optimization used by the processor 200 may be a least-squares optimization.

In some implementations of the disclosed subject matter, the value of the point on the parameterized curve is selected by the processor to be in the predetermined window, such as in the middle of the predetermined window or in any other suitable position.

The processor 200 may estimate parameters of the motion event signal, as well as the noise magnitude estimate of one or more noise signals in the motion event signal, and determine a curve fit error. The processor 200 may determine curve shapes of the motion event signal, the noise signals, and the curve fit error in a time domain. The detection threshold value may be dynamically adjusted by the processor 200 for a determined magnitude and time based on a type of the noise signal.

In some implementations, the processor 200 may clamp a motion signal estimate (e.g., an estimated true motion event signal) by the motion event signal detected by the sensors 71, 72 to avoid overshoot and minimize errors in determining a detection threshold value. The processor 200 may estimate the noise signal shape (e.g., the noise magnitude) as a function of time to be expected when the noise signal is partially identified. The processor 200 may determine an upper bound of the estimated noise magnitude estimate as a function of time, where the upper bound includes the noise signal. The noise signal may, for example, correspond to an electrostatic discharge signal detected by the sensors 71, 72.

In some implementations, the processor 200 may determine the human motion from a filtered motion event signal by subtracting the noise signal to compensate for sensor noise. The processor 200 may raise the detection threshold value when the sensor noise is partially compensated for.

The processor 200 may correlate the determined noise signal with a second data signal from a second sensor (e.g., sensor 72). The processor 200 may estimate a magnitude of the noise signal (e.g., a noise magnitude estimate) and may generate an envelope to dynamically adjust the detection threshold value. The second sensor (e.g., sensor 72) may be an accelerometer, and the determined noise signal is correlated by the processor 200 with jarring of the sensor (e.g., sensor 71) based on accelerometer data from the second sensor (e.g., sensor 72).

The processor 200 may dynamically adjust the detection threshold value when the determined noise signal is based on internal radio transmissions of the sensors 71, 72.

Figure 8A:
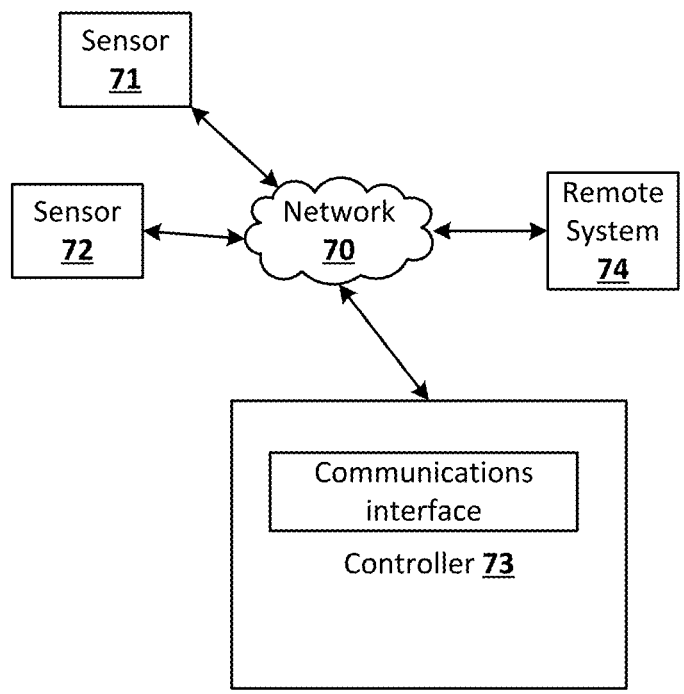
FIGS. 8A-8B show a security system that receives alert communications from a remote system according to an implementation of the disclosed subject matter.
Figure 8B:
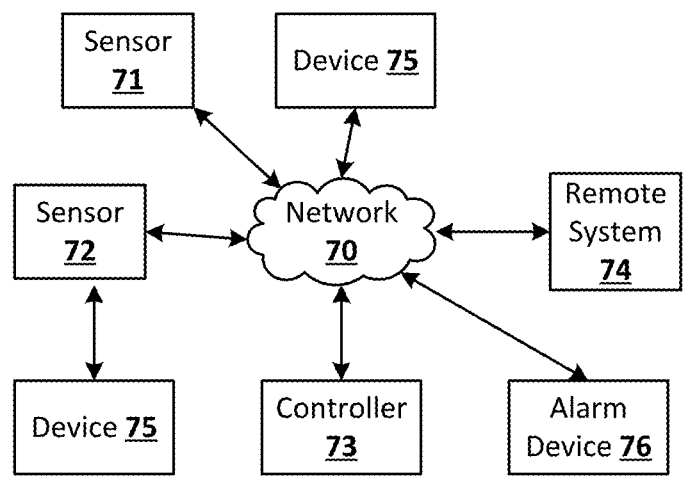

FIGS. 8A-8B show a security system that may include one or more sensors to receive an input signal and filter noise with a processor to determine human movement according to an implementation of the disclosed subject matter. The security system of FIGS. 8A-8B may be used to identify noise sources, and may dynamically adjust an ambient motion threshold of one or more sensors of the security system. The security system may determine a characteristic time signature of one or more noise types (e.g., noise from 6lowpan Tx-coex, ESD, HVAC noise, EMC, LEDs, pets, or the like). The security system may compensate for the noise and may be used to determine a human motion event, such as walking. In some implementations, the security system may transmit a notification, output an alarm, and/or adjust security settings according to a determination of human movement. The security system may, in some implementations, determine when to arm or disarm an alarm device according to detected human motion determined from an input signal to a sensor that may include noise.

The security system shown in FIGS. 8A-8B may include network 70, one or more sensors 71, 72, controller 73 having a communications interface, remote system 74, device 75, and alarm device 76. Sensors 71, 72 will be discussed in detail in connection with FIG. 10, and device 75 will be discussed in detail in connection with FIG. 11.

In some implementations, the security system shown in FIGS. 8A-8B may determine whether the user is located within the home or building (or a predefined area around the home or building), and/or outside of the home. That is, the security system may adjust the security settings according to whether the user is located within the home or outside the home, based in part on the detection of human movement by one or more sensors.

The general features and operation of the security system shown in FIGS. 8A-8B, which may be part of a smart-home environment, are discussed in detail below. The security system may use one or more sensors 71, 72. As used throughout, a sensor may refer to any device that can obtain information about its environment. In implementations of the disclosed subject matter, the sensors may be passive infrared (PIR) sensors that may be used to detect human movement. As discussed throughout, the sensors may identify noise patterns, and may compensate for them so that the sensor and/or processor may determine if there is human movement.

In the security system of FIGS. 8A-8B, the sensors may be described by the type of information they collect. For example, sensor types as disclosed herein may include motion, smoke, carbon monoxide, carbon dioxide, sound, proximity, temperature, time, physical orientation, acceleration, location, entry, presence, and the like. A sensor can include, for example, a camera, a retinal camera, and/or a microphone. Sensors 71, 72 are discussed in detail below in connection with FIG. 10.

The security system of FIGS. 8A-8B and discussed above may be implemented over any suitable wired and/or wireless communication networks, such as network 70. The one or more sensors 71, 72 may communicate via the local network 70, such as a Wi-Fi or other suitable network, with each other and/or with the controller 73. The security system may be communicatively coupled to the remote system 74 via the network 70. As discussed above, the remote system 74 may be a law enforcement communication system, a security service provider system, a neighborhood alert communication system, a weather-related communications system, and/or a social network communication system.

The network 70 may be a mesh-type network such as Thread, which provides network architecture and/or protocols for devices to communicate with one another. Typical home networks may have a single device point of communications. Such networks may be prone to failure, such that devices of the network cannot communicate with one another when the single device point does not operate normally. The mesh-type network of Thread, which may be used in the security system of the disclosed subject matter, may avoid communication using a single device. That is, in the mesh-type network, such as network 70, there is no single point of communication that may fail so as to prohibit devices coupled to the network from communicating with one another.

The communication and network protocols used by the devices communicatively coupled to the network 70 may provide secure communications, minimize the amount of power used (i.e., be power efficient), and support a wide variety of devices and/or products in a home, such as appliances, access control, climate control, energy management, lighting, safety, and security. For example, the protocols supported by the network and the devices connected thereto may have an open protocol which may carry IPv6 natively.

The Thread network, such as network 70, may be easy to set up and secure to use. The network 70 may use an authentication scheme, AES (Advanced Encryption Standard) encryption, or the like to reduce and/or minimize security holes that exist in other wireless protocols. The Thread network may be scalable to connect devices (e.g., 2, 5, 10, 20, 50, 100, 150, 200, or more devices) into a single network supporting multiple hops (e.g., so as to provide communications between devices when one or more nodes of the network is not operating normally). The network 70, which may be a Thread network, may provide security at the network and application layers. One or more devices communicatively coupled to the network 70 (e.g., controller 73, remote system 74, and the like) may store product install codes to ensure only authorized devices can join the network 70. One or more operations and communications of network 70 may use cryptography, such as public-key cryptography.

The devices communicatively coupled to the network 70 of the smart-home environment and/or security system disclosed herein may low power consumption and/or reduced power consumption. That is, devices efficiently communicate to with one another and operate to provide functionality to the user, where the devices may have reduced battery size and increased battery lifetimes over conventional devices. The devices may include sleep modes to increase battery life and reduce power requirements. For example, communications between devices coupled to the network 70 may use the power-efficient IEEE 802.15.4 MAC/PHY protocol. In implementations of the disclosed subject matter, short messaging between devices on the network 70 may conserve bandwidth and power. The routing protocol of the network 70 may reduce network overhead and latency. The communication interfaces of the devices coupled to the smart-home environment may include wireless system-on-chips to support the low-power, secure, stable, and/or scalable communications network 70.

The controller 73 shown in the security system of FIGS. 8A-8B and discussed above may be communicatively coupled to the network 70 and may be and/or include a processor (e.g., processor 200 shown in FIG. 2A). The controller 73 and/or the processor 200 may identify noise sources from one or more signals received from the sensors 71, 72, and may compensate for the identified noise so as to determine whether a human motion event has occurred.

Alternatively, or in addition, the controller 73 may be a general- or special-purpose computer. The controller 73 may receive, aggregate, and/or analyze alert communications received from the remote system 74 via the network 70. The controller 73 may also receive, aggregate, and/or analyze environmental information received from the sensors 71, 72. The sensors 71, 72 and the controller 73 may be located locally to one another, such as within a single dwelling, office space, building, room, or the like, or they may be remote from each other, such as where the controller 73 is implemented in a remote system 74 such as a cloud-based reporting and/or analysis system.

Alternatively or in addition, sensors 71, 72 may communicate directly with the remote system 74. In this example, the remote system 74 may aggregate data from multiple locations, provide instruction, software updates, and/or aggregated data to a controller 73 and/or sensors 71, 72. In another example, the remote system 74 may aggregate data from the sensors 71, 72, may analyze the aggregated data, and transmit an alert communication to a user device (e.g., device 75) and/or other security systems coupled to the remote system 74 (e.g., other devices that are coupled to and/or have registered with the remote system 74).

The sensor network that may include sensors 71, 72 shown in FIGS. 8A-8B may be an example of a smart-home environment. The depicted smart-home environment may include a structure, a house, office building, garage, mobile home, or the like. The devices of the smart home environment, such as the sensors 71, 72, the controller 73, and the network 70 may be integrated into a smart-home environment that does not include an entire structure, such as an apartment, condominium, or office space.

The smart-home environment can control and/or be coupled to devices outside of the structure. For example, one or more of the sensors 71, 72 may be located outside the structure, for example, at one or more distances from the structure (e.g., sensors 71, 72) may be disposed outside the structure, at points along a land perimeter on which the structure is located, and the like. One or more of the devices in the smart home environment need not physically be within the structure. For example, the controller 73 which may receive input from the sensors 71, 72 may be located outside of the structure.

The structure of the smart-home environment may include a plurality of rooms, separated at least partly from each other via walls. The walls can include interior walls or exterior walls. Each room can further include a floor and a ceiling. Devices of the smart-home environment, such as the sensors 71, 72, may be mounted on, integrated with and/or supported by a wall, floor, or ceiling of the structure.

The smart-home environment including the sensor network shown in FIGS. 8A-8B may include a plurality of devices, including intelligent, multi-sensing, network-connected devices, which can integrate seamlessly with each other and/or with a central server or a cloud-computing system (e.g., controller 73 and/or remote system 74) to provide home-security and smart-home features. The smart-home environment may include one or more intelligent, multi-sensing, network-connected thermostats (e.g., "smart thermostats"), one or more intelligent, network-connected, multi-sensing hazard detection units (e.g., "smart hazard detectors"), and one or more intelligent, multi-sensing, network-connected entryway interface devices (e.g., "smart doorbells"). The smart hazard detectors, smart thermostats, and smart doorbells may be the sensors 71, 72 shown in FIGS. 8A-8B.

For example, a smart thermostat may detect ambient climate characteristics (e.g., temperature and/or humidity) and may control an HVAC (heating, ventilating, and air conditioning) system accordingly of the structure. For example, the ambient client characteristics may be detected by sensors 71, 72 shown in FIGS. 8A-8B, and the controller 73 may control the HVAC system (not shown) of the structure.

As another example, a smart hazard detector may detect the presence of a hazardous substance or a substance indicative of a hazardous substance (e.g., smoke, fire, or carbon monoxide). For example, smoke, fire, and/or carbon monoxide may be detected by sensors 71, 72 shown in FIGS. 8A-8B, and the controller 73 may control an alarm system to provide a visual and/or audible alarm to the user of the smart-home environment.

As another example, a smart doorbell may control doorbell functionality, detect a person's approach to or departure from a location (e.g., an outer door to the structure), and announce a person's approach or departure from the structure via audible and/or visual message that is output by a speaker and/or a display coupled to, for example, the controller 73.

In some implementations, the smart-home environment of the sensor network shown in FIGS. 8A-8B may include one or more intelligent, multi-sensing, network-connected wall switches (e.g., "smart wall switches"), one or more intelligent, multi-sensing, network-connected wall plug interfaces (e.g., "smart wall plugs"). The smart wall switches and/or smart wall plugs may be or include one or more of the sensors 71, 72 shown in FIGS. 8A-8B. A smart wall switch may detect ambient lighting conditions, and control a power and/or dim state of one or more lights. For example, a sensor such as sensors 71, 72, may detect ambient lighting conditions, and a device such as the controller 73 may control the power to one or more lights (not shown) in the smart-home environment. Smart wall switches may also control a power state or speed of a fan, such as a ceiling fan. For example, sensors 72, 72 may detect the power and/or speed of a fan, and the controller 73 may adjusting the power and/or speed of the fan, accordingly. Smart wall plugs may control supply of power to one or more wall plugs (e.g., such that power is not supplied to the plug if nobody is detected to be within the smart-home environment). For example, one of the smart wall plugs may controls supply of power to a lamp (not shown).

In implementations of the disclosed subject matter, a smart-home environment may include one or more intelligent, multi-sensing, network-connected entry detectors (e.g., "smart entry detectors"). Such detectors may be or include one or more of the sensors 71, 72 shown in FIGS. 8A-8B. The illustrated smart entry detectors (e.g., sensors 71, 72) may be disposed at one or more windows, doors, and other entry points of the smart-home environment for detecting when a window, door, or other entry point is opened, broken, breached, and/or compromised. The smart entry detectors may generate a corresponding signal to be provided to the controller 73 and/or the remote system 74 when a window or door is opened, closed, breached, and/or compromised. In some implementations of the disclosed subject matter, the alarm system, which may be included with controller 73 and/or coupled to the network 70 may not arm unless all smart entry detectors (e.g., sensors 71, 72) indicate that all doors, windows, entryways, and the like are closed and/or that all smart entry detectors are armed.

The smart-home environment of the sensor network shown in FIGS. 8A-8B can include one or more intelligent, multi-sensing, network-connected doorknobs (e.g., "smart doorknob"). For example, the sensors 71, 72 may be coupled to a doorknob of a door (e.g., doorknobs 122 located on external doors of the structure of the smart-home environment). However, it should be appreciated that smart doorknobs can be provided on external and/or internal doors of the smart-home environment.

The smart thermostats, the smart hazard detectors, the smart doorbells, the smart wall switches, the smart wall plugs, the smart entry detectors, the smart doorknobs, the keypads, and other devices of a smart-home environment (e.g., as illustrated as sensors 71, 72 of FIGS. 8A-8B can be communicatively coupled to each other via the network 70, and to the controller 73 and/or remote system 74 to provide security, safety, and/or comfort for the smart home environment).

A user can interact with one or more of the network-connected smart devices (e.g., via the network 70). For example, a user can communicate with one or more of the network-connected smart devices using a computer (e.g., a desktop computer, laptop computer, tablet, or the like) or other portable electronic device (e.g., a smartphone, smart watch, wearable computing device, a tablet, a key FOB, a radio frequency and the like). A webpage or application can be configured to receive communications from the user and control the one or more of the network-connected smart devices based on the communications and/or to present information about the device's operation to the user. For example, the user can view the webpage and/or the application, and can arm or disarm the security system of the home.

One or more users can control one or more of the network-connected smart devices in the smart-home environment using a network-connected computer or portable electronic device. In some examples, some or all of the users (e.g., individuals who live in the home) can register their mobile device and/or key FOBs with the smart-home environment (e.g., with the controller 73). Such registration can be made at a central server (e.g., the controller 73 and/or the remote system 74) to authenticate the user and/or the electronic device as being associated with the smart-home environment, and to provide permission to the user to use the electronic device to control the network-connected smart devices and the security system of the smart-home environment. A user can use their registered electronic device to remotely control the network-connected smart devices and security system of the smart-home environment, such as when the occupant is at work or on vacation. The user may also use their registered electronic device to control the network-connected smart devices when the user is located inside the smart-home environment.

Alternatively, or in addition to registering electronic devices, the smart-home environment may make inferences about which individuals live in the home and are therefore users and which electronic devices are associated with those individuals. As such, the smart-home environment may "learn" who is a user (e.g., an authorized user) and permit the electronic devices associated with those individuals to control the network-connected smart devices of the smart-home environment (e.g., devices communicatively coupled to the network 70), in some implementations including sensors used by or within the smart-home environment. The smart-home environment may provide notifications to users when there is an attempt to use network-connected smart devices in a manner that is atypical from the learned pattern of usage. Various types of notices and other information may be provided to users via messages sent to one or more user electronic devices. For example, the messages can be sent via email, short message service (SMS), multimedia messaging service (MMS), unstructured supplementary service data (USSD), as well as any other type of messaging services and/or communication protocols.

A smart-home environment may include communication with devices outside of the smart-home environment but within a proximate geographical range of the home. For example, the smart-home environment may include an outdoor lighting system (not shown) that communicates information through the communication network 70 or directly to a central server or cloud-computing system (e.g., controller 73 and/or remote system 74) regarding detected movement and/or presence of people, animals, and any other objects and receives back commands for controlling the lighting accordingly.

The controller 73 and/or remote system 74 can control the outdoor lighting system based on information received from the other network-connected smart devices in the smart-home environment. For example, in the event any of the network-connected smart devices, such as smart wall plugs located outdoors, detect movement at night time, the controller 73 and/or remote system 74 can activate the outdoor lighting system and/or other lights in the smart-home environment.

In implementations of the disclosed subject matter, the remote system 74 shown in FIGS. 8A-8B may be a law enforcement provider system, a home security provider system, a medical and/or emergency services provider system, and/or a fire department provider system. When a security event and/or environmental event is detected by at least one of one sensors 71, 72, a message may be transmitted to the remote system 74. The content of the message may be according to the type of security event and/or environmental event detected by the sensors 71, 72. For example, if smoke is detected by one of the sensors 71, 72, the controller 73 may transmit a message to the remote system 74 associated with a fire department to provide assistance with a smoke and/or fire event (e.g., request fire department response to the smoke and/or fire event). Alternatively, the sensors 71, 72 may generate and transmit the message to the remote system 74. In another example, when one of the sensors 71, 72 detects a security event, such a window or door of a building being compromised, a message may be transmitted to the remote system 74 associated with local law enforcement to provide assistance with the security event (e.g., request a police department response to the security event).

The controller 73 and/or the remote system 74 may include a display to present an operational status message (e.g., an alert communication, a security event, an environmental event, an operational condition, or the like). For example, the display of the controller 73 and/or remote system 74 may display the operational status message to a user while the user is away from the building having the security system disclosed herein. Alternatively, or in addition, the controller 73 may display the operational status message to a user when the user arrives at and/or departs (i.e., exits) from the building. For example, one or more sensors may identify and authenticate the user (e.g., using images captured by the sensor, and comparing them with pre-stored images, and/or according to identifying information from the device of a user, such as a smartphone, smart watch, wearable computing device, key FOB, RFID tag, or the like), and the security system may display the operational status message.

FIG. 8B shows a security system that includes an alarm device 76, which may include a light and an audio output device. The alarm device 76 may be controlled, for example, by controller 73 when one or more sensors 71, 72 detect a security event and/or an environmental event. In some implementations, the security event may be human motion that is detected by the sensors 71, 72 and as determined by the processor 200 and/or controller 73. The light of the alarm device 76 may be activated so as to be turned on when one or more sensors 71, 72 detect a security event and/or an environmental event. Alternatively, or in addition, the light may be turned on and off in a pattern (e.g., where the light is turned on for one second, and off for one second; where the light is turned on for two seconds, and off for one second, and the like) when one or more sensors 71, 72 detect a security event and/or an environmental event. Alternatively, or in addition, an audio output device of the alarm device 76 may include at least a speaker to output an audible alarm when a security event and/or an environmental event is detected by the one or more sensors 71, 72. For example, a security event may be when one or more sensors 71, 72 are motion sensors that detect motion either inside a building having the security system disclosed herein, or within a predetermined proximity to the building. The speaker of the alarm device 76 may, for example, output a message when the user arrives at the building or departs from the building according to the operational status of the security system (e.g., a security and/or environmental event has been detected, an operational issue with the security system has been detected, the security system has been armed and/or disarmed, or the like).

FIG. 8B shows a device 75 that may be communicatively coupled to a sensor. Although FIG. 8B illustrates that device 75 is coupled to sensor 72, the device 75 may be communicatively coupled to sensor 71 and/or sensor 72. The device 75 may be a computing device as shown in FIG. 6 and described below, and/or a key FOB. A user of the security system disclosed herein may control the device 75. When the device 75 is within a predetermined distance (e.g., one foot, five feet, 10 feet, 20 feet, 100 feet, or the like) from the sensor 72, the device 75 and the sensor 72 may communicate with one another via Bluetooth signals, Bluetooth Low Energy (BTLE) signals, Wi-Fi pairing signals, near field communication (NFC) signals, radio frequency (RF) signals, infra-red signals, and/or short-range communication protocol signals. For example, the user may present the device 75 within the predetermined distance range of the sensor so that the device 75 and the sensor may communicate with one another. The device 75 may provide identifying information to the sensor 72, which may be provided to the controller 73 to determine whether the device 75 belongs to an authorized user of the security system disclosed herein.

The controller 73 may monitor the location of the device 75 in order to determine whether to arm or disarm the alarm device 76. The controller 73 may arm or disarm the alarm device 76 according to, for example, whether the device 75 is within a home, building, and/or a predetermined area. The predetermined area may be defined, for example, according to, for example, geo-fencing data, placement and/or range of sensors 71, 72, a defined distance from the building having the security system disclosed herein, and the like.

In example implementations of the disclosed subject matter, the device 75 may be associated with an authorized user. Authorized users may be those users, for example, who have identifying information stored and/or registered with the controller 73. Identifying information may include, for example, images of the user, voice recordings of the user, identification codes that are stored in a user's device, user PIN codes, and the like.

For example, when the authorized user and the device 75 are outside of the home, building, and/or predetermined area, the controller 73 may arm the alarm device 76. In determining whether to arm the alarm device 76, the controller may gather data from the sensors 71, 72, to determine whether any other person is in the building. When the alarm device 76 is armed, and the user and the device 75 return to the home, building, and/or predetermined area of the security system, the controller 73 may disarm the alarm device 76 according to the signals received by the sensors 71, 72 from the device 75. The exchanged signals may include the identifying information of the user.

In FIGS. 8A-8B, the sensor 71, 72 may be a camera to capture an image of a face of a person to be transmitted to the controller 73, where the controller 73 compares the captured facial image with a pre-stored image. When it is determined by the controller 73 that at least a portion of the captured facial image matches the pre-stored image, the controller 73 determines that the person is an authorized user of the security system disclosed herein. The controller 73 may arm or disarm the alarm device 76 according to the determination of whether the person is an authorized user.

The sensor 71, 72 may be a camera to capture a retinal image from a person to be transmitted to the controller 73, where the controller 73 compares the captured retinal image with a pre-stored image. When it is determined by the controller 73 that at least a portion of the captured retinal image matches the pre-stored image, the controller 73 determines that the person is an authorized user of the security system disclosed herein. The controller 73 may arm or disarm the alarm device 76 according to the determination of whether the person is an authorized user.

The sensor 71, 72 may be a microphone to capture a voice of a person to be transmitted to the controller 73, where the controller 73 compares the captured voice with a pre-stored voice. When it is determined by the controller 73 that at least a portion of the captured voice matches the pre-stored voice, the controller 73 determines that the person is an authorized user of the security system disclosed herein.

When the sensor 72 and/or the controller 73 determine that the device 75 is associated with an authorized user according to the transmitted identification information, the sensor 72 and/or the controller 73 provide an operational status message to the user via a speaker (i.e., audio output 77), a display (e.g., where the display is coupled to the controller 73 and/or remote system 74), and/or the device 75. The operational status message displayed can include, for example, an alert communication and/or a message that a security event and/or environmental event has occurred. When the sensors 71, 72 have not detected a security and/or environmental event, a message may be displayed that no security and/or environmental event has occurred. When the controller 73 has not received an alert communication from the remote system 74, a message may be displayed that no alert communication has been received. In implementations of the subject matter disclosed herein, the device 75 may display a source of the security event and/or environmental event, a type of the security event and/or environmental event, a time of the security event and/or environmental event, and a location of the security event and/or environmental event. In some implementations, the device 75 may display the alert communication, and may include information about the alert (e.g., the cause of the alert, the source of the alert, and the like).

In implementations of the disclosed subject matter, the device 75 may be communicatively coupled to the network 70 so as to exchange data, information, and/or messages with the sensors 71, 72, the controller 73, and the remote system 74. The device is discussed below in further detail in connection with FIG. 11.

In implementations of the disclosed subject matter, the controller 73 can request entry of an access code from the device 75 and/or a keypad communicatively coupled to the controller 73. Upon receipt of the access code, the security system disclosed herein may be disarmed, and/or may provide an operational status message to the user via a display coupled to the controller 73 and/or the device 75. Alternatively, or in addition, an operational status message may be output via a speaker of the alarm device 76. In some implementations, the operation status message may include an alert communication, and/or whether an alert communication has been received.

For example, a preset time (e.g., 15 seconds, 30 seconds, 1 minute, 5 minutes, or the like) may be set for the security system to allow for a user to exit the home or building before arming the alarm device 76. A preset time may be set for the security system to allow for a user to enter the home and disarm the alarm device 76. In some implementations, when an alert communication is received, the preset time for entry may be reduced.

The preset time for entry of the home and the preset time to exit the home may be the same amount of time, or can be set to provide different amounts of time. If a user needs more time to enter or exit the home with the security system, an electronic device of the user (e.g., a smartphone, smart watch, wearable computing device, radio frequency identification (RFID) tag, fitness band or sensor, a key FOB, or the like, such as device 75) can request, upon receiving input from the user, that the controller 73 provide additional time beyond the preset time to allow for the user to enter or exit the home. Alternatively, or in addition, the security system disclosed herein may extend the preset time to enter or exit. For example, the time may be extended for exiting the home while the user and/or the user's electronic device are in the home. That is, the sensors 71, 72 may determine that the user and/or the user's registered electronic device are in the home and are engaged in moving towards exiting, and the controller 73 may extend the preset time to exit. Alternatively, or in addition, the device 75 may transmit a command (e.g., when input is received from the user) to the controller 73 to disengage the exit process (e.g., the controller 73 and/or the alarm device 76 are disengaged from counting down the preset time before arming the alarm device 76).

In another example, when the user returns home, a preset time for entry to disarm the alarm device 76 may be extended according to whether the user has an electronic device (e.g., device 75, which may be a smartphone, smart watch, wearable computing device, RFID tag, fitness band or sensor, key FOB, or the like) that is registered with the controller 73. That is, the sensors, 71, 72 may detect the presence of the device 75 with the user, and may disarm the alarm device 76. When the sensors 71, 72 determine that the user does not have the device 75, the controller 73 may extend the preset time so that a user may be given additional time to enter a code on, for example, a keypad communicatively coupled to the controller 73, to disarm the alarm device 76.

In another example, when an alert communication is received by controller 73 from the remote system 74, the controller 73 may reduce the preset time. In some implementations, the user may accept or decline the change to the setting of the security system via the device 75 when the alert communication and/or a settings change notification is displayed on the device 75.

As illustrated in FIGS. 8A-8B, a security system can include sensors (e.g., sensors 71, 72) to detect a location of at least one user, and generate detection data according to the detected location of at least one user of the security system. As discussed above, the sensor 71, 72 may be used to detect human movement. The detection data may be generated by the sensors 71, 72. For example, the at least one user may be one or more members of a household, and the security system may monitor their location using the sensors 71, 72 to determine whether to arm or disarm the alarm device 76. A processor, such as the processor 200 shown in FIG. 2A and/or the controller 73 illustrated in FIGS. 8A-8B and described above, may be communicatively coupled to the sensors 71, 72, and can receive the detection data. The processor 200 and/or the controller 73 can determine whether the at least one user is occupying a home, building, and/or within a predetermined area according to the detection data. The predetermined area may be set according to the boundaries of a home or building, geofencing data, motion data, a door position event, a distance from one or more sensors, and the like.

In determining the location of a user, the sensors 71, 72 can detect the location of one or more electronic devices (e.g., device 75) associated with a user. The one or more devices may be registered with the controller 73 and/or the remote system 74. As discussed above, sensors 71, 72 may communicate with another via Bluetooth signals, Bluetooth Low Energy (BTLE) signals, Wi-Fi pairing signals, near field communication (NFC) signals, radio frequency (RF) signals, infra-red signals, and/or short-range communication protocol signals. The device 75 may provide identifying information to the sensor 72, which may be provided to the controller 73 and/or the remote system 74 to determine whether the device 75 belongs to an authorized user of the security system disclosed herein. When the controller 73 and/or the remote system 74 determine that the device is an authorized device of the user, the controller 73 and/or the remote system 74 may determine the location of the device 75.

The sensors 71, 72 may be used determine whether the user associated with the device 75 can be identified with the device. For example, the sensors 71, 72 can determine whether an authorized user has a physical presence with the registered device (e.g., device 75), or whether an unauthorized person has possession of an authorized device. For example, as discussed above, a sensor 71, 72 having a camera can capture an image to determine if an authorized user has possession of the located device 75.

In some implementations, the sensors 71, 72 can detect motion of the user and/or whether a location of the user is outside of the home, building, and/or predetermined area. The sensors 71, 72 may determine whether a user's first electronic device (e.g., a smartphone, smart watch, wearable computing device, or the like) is within the home, building, and/or predetermined area. The controller 73 can determine whether to arm the alarm device 76 according one a location of a user's second electronic device (e.g., a key FOB, RFID tag, fitness band or sensor, or the like), geofencing data, and the detection data from the sensors 71, 72.

The security system disclosed herein includes an alarm device, such as the alarm device 76 illustrated in FIG. 8B and discussed above, which can be armed or disarmed by the controller 73 according to the determination as to whether the at least one user is occupying the home or building, and/or within the predetermined area.

For example, if the controller 73 determines that the members of a household (e.g., the users of the home security system) have exited the house (e.g., are no longer occupying the home or building, and are outside of the predetermined area), the controller 73 may arm the alarm device 76. After exiting, controller 73 may request confirmation from the user, via the device 75, to arm the alarm. The sensors 71, 72 may determine the location of the members of the household according to their respective electronic devices (e.g., smartphones, smart watch, wearable computing device, tablet computers, key FOBs, RFID tag, fitness band or sensor, and the like), according to images captured by the sensors, according to the sensors detecting one or more doors opening and closing, and the like.

For example, the sensors 71, 72 may detect one or more doors opening and/or closing, the processor 200 and/or the controller 73 may determine an approximate location of a user, according to the location of the sensor for the door, and what direction the door was opened and/or closed in. The data generated by the door sensors 71, 72 regarding the directional opening of the door, as well as the location of the sensor, may be used along with other sensor data from sensors 71, 72 (e.g., motion data, camera images, sound data, and/or thermal data, and the like) to provide an improved location determination of the user.

The controller 73 may aggregate detection data from the sensors 71, 72 and store it in a storage device coupled to the controller 73 or the network 70. The data aggregated by the controller 73 may be used to determine entrance and exit patterns (e.g., what days and times users enter and exit from the house, what doors are used, and the like) of the members of the household, and the controller 73 may arm or disarm the alarm device 76 according to the determined patterns.

In implementations of the disclosed subject matter, one or more user electronic devices (e.g., device 75) can be registered with the controller 73, and the at least one of the sensors 71, 72 transmits a location request signal to the device 75. In response to the location request signal, the device 75 can transmits a location signal, and the controller 73 can determine the location of the device 75 according to the received location signal. The location request signal and the location signal can be Bluetooth signals, Bluetooth Low Energy (BTLE) signals, radio frequency (RF) signals, near field communications (NFC) signals, and the like.

The controller 73 can transmit a request message to be displayed by the device 75. The message may be, for example, a reminder to arm or disarm the alarm device 76. In some implementations, the message may include information about a received alert communication, and/or changes to the settings of the security system in response to the received alert communication. Upon displaying the message the electronic device receives input to arm or disarm the alarm device 76 according to the displayed request message, and transmits the received input to the controller 73 so as to control the alarm device 76. When an alert communication has been received, additional information may be requested, such as a PIN, security code or the like. For example, the controller can request a code from the user to either arm or disarm the alarm device 76. When the user provides the code to the device 75, which correspondingly transmits the entered code to the controller 73, the controller 73 may control the arming or disarming of the alarm device 76. Alternatively, or in addition, the controller 73 can control the alarm device 76 to be automatically armed when the user is no longer occupying the home or building, and/or is outside of the predetermined area. Alternatively, or in addition, the controller may control the arming or disarming of the alarm device 76 according to a code that entered in a keypad that is communicatively coupled to the controller 73.

In implementations of the disclosed subject matter, authentication requirements for arming or disarming of the alarm device 76 may be reduced when a device 75 is used to arm or disarm, and the device 75 is a registered device. When a button on the registered device 75 or displayed by the device 75 is used to arm or disarm the alarm device 76, the user may not have to enter a code, a shortened PIN code, a voice code, or the like. As discussed above, in some implementations, authentication requirements for disarming the alarm device 75 may be increased when an alert communication is received by the security system.

When the sensors 71, 72 for an entry door to the home or building become disconnected from the network 70 and the controller 73, and the alarm device 76 is armed, the user may still re-enter the home. The security system may learn which doors are used by the user to enter and/or exit a home. The sensors 71, 72 associated with the doors that are used to enter and/or exit the home may store identifying information, so that the user may present a device 75 to the sensors 71, 72 to exchange identifying information to allow the user to enter the door. Once the user enters, the user may manually disarm the alarm device 76 by entering a security code. In some implementations, such as when an alert communication is received, the time permitted to manually disarm the alarm device 76 may be reduced.

The security system may learn the how the user typically arms and disarms the alarm device 76 (e.g., using a keypad, using the device 75, allowing for auto-arming, or the like). The device 75 may receive a message from the controller 73 when there is an attempt to disarm the alarm device 76 at a time of day and/or in a manner that is inconsistent with a user history or pattern for disarming. The controller 73 may request that the user of device 75 confirm whether the disarming is authorized, and may provide information from sensors 71, 72 (e.g., images captured of the person attempting the disarming) to assist in the confirmation. Via the device 75, the user may confirm or deny the request by the controller 73 to disarm the alarm device.

In implementations of the disclosed subject matter, the alarm device 76 can be armed or disarmed by the controller 73 according to geo-location data from the sensors 71, 72 and/or the device 75. For example, if the sensors 71, 72 determine that the device 75 is physically located with an authorized user (e.g., as discussed above) according to geo-location data received from the device 75, and the user has exited the home and there are no other users in the home according to the sensors 71, 72, the controller 73 can automatically arm the alarm device. Alternatively, the controller may transmit a request message to the device 75 to determine if the user would like to arm the alarm device 76. For example, the message may display a selectable button to arm or disarm the alarm device 76. In another example, one or more sensors 71, 72 may determine the geo-location of an authorized user who is exiting the home, and may determine that one or more users are still located in the home according to geo-location data, and the controller 73 may refrain from arming the alarm device 76 to allow for the one or more users still in the home to exit. In yet another example, the sensors 71, 72 may determine the geo-location of an authorized user who has exited the home, and determine that one or more users are still located within the home, and the controller 73 may automatically arm the alarm device 76 to activate an audio and/or visual alarm when a defined outer perimeter is breached by an unauthorized user or when a door leading outside of the home is opened, but may not activate the alarm when doors internal to the home are opened or closed.

In some implementations, when an alert communication has been received by the security system, the alarm device 76 disarmed by the controller 73 according to a PIN, a security code, and/or other access information provided by the device 75.

In some implementations, the alarm device 76 can be armed or disarmed when the controller 73 determines that the device 75 and/or sensors 71, 72 are disconnected from the communications network 70 coupled to the alarm device 76. For example, if device 75 and/or sensors 71, 72 are disconnected from the network 70 so as to be decoupled from the controller 73 and/or remote system 74, the controller 73 may arm the alarm device 76. That is, the network 70 may be a wireless network having a predetermined communicative range within and/or around the perimeter of a house or building. When an authorized device 75 becomes decoupled from the network 70 (e.g., because the device 75 is outside of the predetermined communicative range) and/or the sensors 71, 72 become decoupled from the network 70, the controller 73 may automatically arm the alarm device 76.

In the security system disclosed herein, sensors 71, 72 can detect a security event, such as human motion, a door event (e.g., where a door to a house is opened, closed, and/or compromised) or a window event (e.g., where a window of a house is opened, closed, and/or compromised). For example, the sensors 71, 72 may determine human motion within the house when no was expected, and controller 73 and/or processor 200 may identify the motion as a compromising event. In another example, the sensors 71, 72 may have an accelerometer that identifies the force on the door or window as a compromising event. In another example, the sensors 71, 72 may contain an accelerometer and/or compass, and the compromising event may dislodge the sensor from the door or window, and the motion of the sensor 71, 72 may identify the motion as a compromising event. The controller 73 may activate the alarm device 76 according to whether the detected door event or window event is from an outside location (e.g., outside the house, building, or the like). That is, the controller 73 may control the alarm device 76 to output an audible alarm and/or message via a speaker when a door event or window event is detected by the sensors 71, 72. A light of the alarm device 76 may be activated so as to be turned on when one or more sensors 71, 72 detect a security event, such as a motion event, a door event, or a window event. Alternatively, or in addition, a light may be turned on and off in a pattern (e.g., where the light is turned on for one second, and off for one second; where the light is turned on for two seconds, and off for one second, and the like) when one or more sensors 71, 72 detect a security event such as the window and/or door event.

The controller 73 can control the alarm device 76 to be armed or disarmed according to a preset time period for a user to enter or exit a home or building associated with the security system. The predetermined time can be adjusted by the controller 73 and/or according to the user. For example, as discussed herein, the processor 200 and/or the controller 73 can aggregate data from the sensors 71, 72 to determine human motion, such as when a user enters and exits the home (e.g., the days and times for entry and exit, the doors associated with the entry and exit, and the like). For example, the controller 73 can adjust the amount of time for arming the alarm device 76 to be longer or shorter, according to the amount of time the user takes to exit the house according to the aggregated data. In some implementations, when an alert communication is received by the security system, the controller 73 may reduce the preset time allotted for a user to enter a home.

In the security system disclosed herein the at least one sensor determines that the user is not occupying the home or building, and/or is outside of the predetermined area for a time greater than a preset time, the controller 73 can control the alarm device 76 to transition from a first security mode to a second security mode. The second security mode may provide a higher level of security than the first security mode. For example, the second security mode may be a "vacation" mode, where the user of the security system disclosed herein (e.g., the members of a household) are away from the house for a period of time (e.g., 1 day, 3 days, 5 days, 1 week, 2 weeks, 1 month, or the like). As discussed herein, the controller 73 may aggregate the detection data received from the sensors 71, 72 over a preset time (e.g., 1 week, 1 month, 6 months, 1 year, or the like) to determine a pattern for when the user is within the predetermined location or not. In some implementations, the controller 73 may control the alarm device 76 to transition from the first security mode to the second security mode when an alert communication is received by the security system. That is, the security system may provide a higher level of security in the second mode when the alert communication is received.

Figure 9:
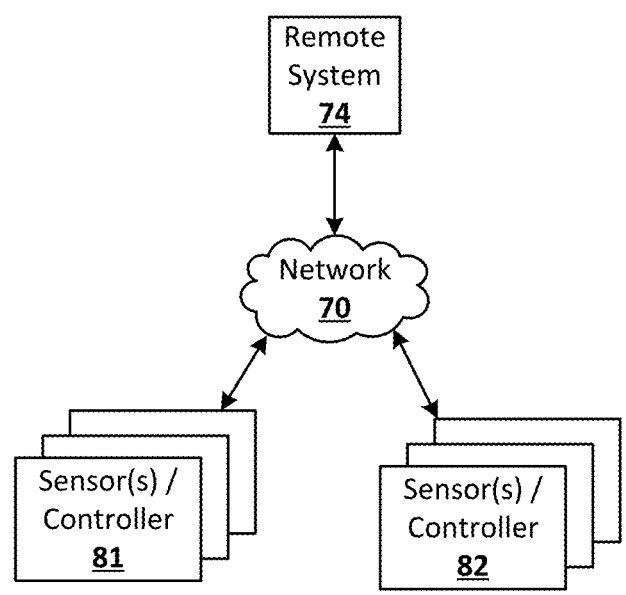
FIG. 9 shows a remote system to aggregate data from multiple locations having security systems according to an implementation of the disclosed subject matter.

In some configurations, as illustrated in FIG. 9, a remote system 74 may aggregate data from multiple locations, such as multiple buildings, multi-resident buildings, and individual residences within a neighborhood, multiple neighborhoods, and the like. In some implementations, the remote system 74 in FIG. 9 may be different from the law enforcement communication system, the security service provider system, the neighborhood alert communication system, and/or the social network communication system of the remote system 74 shown in FIGS. 8A-8B. In general, multiple sensor/controller systems 81, 82 as previously described with respect to FIGS. 8A-8B may provide information to the remote system 74. The systems 81, 82 may provide data directly from one or more sensors as previously described, or the data may be aggregated and/or analyzed by local controllers such as the controller 73, which then communicates with the remote system 74. The remote system may aggregate and analyze the data from multiple locations, and may provide aggregate results to each location. For example, the remote system 74 may examine larger regions for common sensor data or trends in sensor data, and provide information on the identified commonality or environmental data trends to each local system 81, 82.

For example, remote system 74 may gather and/or aggregate security event and/or environmental event data from systems 81, 82, which may be geographically proximally located to the security system illustrated in FIGS. 8A-8B. The systems 81, 82 may be located within one-half mile, one mile, five miles, ten miles, 20 miles, 50 miles, or any other suitable distance from the security system of a user, such as the security system shown in FIGS. 8A-8B. The remote system 74 may provide at least a portion of the gathered and/or aggregated data to the controller 73 and/or the device 75 illustrated in FIG. 8B. In some implementations, the remote system 74 may gather and/or aggregate alert communications and provide them to systems 81, 82.

The user of the device 75 may receive information from the controller 73 and/or the remote system 74 regarding a security event that is geographically proximally located to the user of the device 75 and/or the security system of a building (e.g., a home, office, or the like) associated with the user. Alternatively, or in addition, an application executed by the device 75 may provide a display of information from systems 81, 82, and/or from the remote system 74.

For example, an unauthorized entry to a building associated with systems 81, 82 may occur, where the building is within one-half mile from the building associated with the user of the device 75. The controller 73 and/or the remote system 74 may transmit a message (e.g., a security alert message) to the device 75 that an unauthorized entry has occurred in a nearby building, thus alerting the user to security concerns and/or potential security threats regarding their geographically proximally located building. In some implementations, the remote system 74 may transmit an alert communication to a user device that an unauthorized entry has occurred in the area.

In another example, a smoke and/or fire event of a building associated with systems 81, 82 may occur, where the building is within 500 feet from the building associated with the user of the device 75. The controller 73 and/or the remote system 74 may transmit a message (e.g., a hazard alert message, an alert communication message) to the device 75 that the smoke and/or fire event has occurred in a nearby building, thus alerting the user to safety concerns, as well as potential smoke and/or fire damage to their geographically proximally located building.

In situations in which the systems discussed here collect personal information about users, or may make use of personal information, the users may be provided with an opportunity to control whether programs or features collect user information (e.g., a user's current location, a location of the user's house or business, or the like), or to control whether and/or how to receive content from the content server that may be more relevant to the user. In addition, certain data may be treated in one or more ways before it is stored or used, so that personally identifiable information is removed. For example, specific information about a user's residence may be treated so that no personally identifiable information can be determined for the user, or a user's geographic location may be generalized where location information is obtained (such as to a city, ZIP code, or state level), so that a particular location of a user cannot be determined. As another example, systems disclosed herein may allow a user to restrict the information collected by those systems to applications specific to the user, such as by disabling or limiting the extent to which such information is aggregated or used in analysis with other information from other users. Thus, the user may have control over how information is collected about the user and used by a system as disclosed herein.

Figure 10:
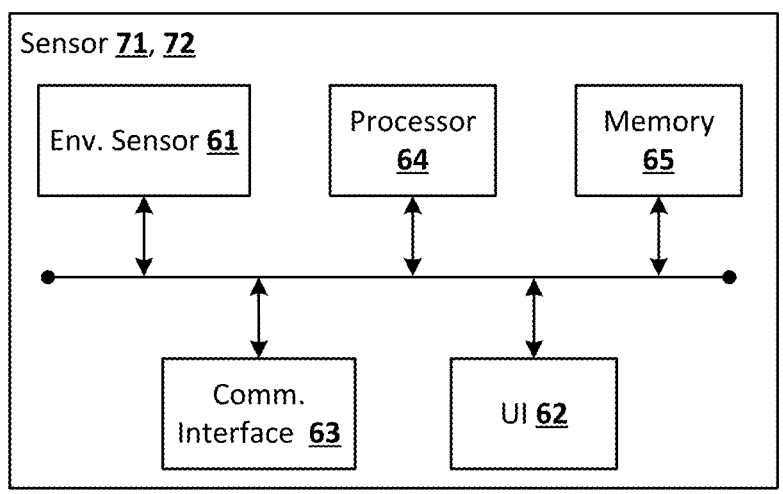
FIG. 10 shows an example sensor according to an implementation of the disclosed subject matter.

FIG. 10 shows an example sensor (e.g., a PIR sensor) that may be used in one or more of the implementations shown in FIGS. 2A-2B and 8A-8B. As shown in FIG. 10, the sensor may include hardware in addition to the specific physical sensor that obtains information about the environment.

A sensor, as used throughout, may be described in terms of the particular physical device that obtains the environmental information. For example, a PIR sensor may obtain motion information, which may be used to determine whether there is human motion (e.g., a walking motion or the like). In another example, an accelerometer may obtain acceleration information, and thus may be used as a general motion sensor and/or an acceleration sensor. A sensor also may be described in terms of the specific hardware components used to implement the sensor. For example, a temperature sensor may include a thermistor, thermocouple, resistance temperature detector, integrated circuit temperature detector, or combinations thereof. A sensor also may be described in terms of a function or functions the sensor performs within an integrated sensor network, such as a smart home environment as disclosed herein. For example, a sensor may operate as a security sensor when it is used to determine security events such as unauthorized entry. A sensor may operate with different functions at different times, such as where a motion sensor is used to control lighting in a smart home environment when an authorized user is present, and is used to alert to unauthorized or unexpected movement when no authorized user is present, or when an alarm system is in an "armed" state, or the like. In some cases, a sensor may operate as multiple sensor types sequentially or concurrently, such as where a temperature sensor is used to detect a change in temperature, as well as the presence of a person or animal. A sensor also may operate in different modes at the same or different times. For example, a sensor may be configured to operate in one mode during the day and another mode at night. As another example, a sensor may operate in different modes based upon a state of a home security system or a smart home environment, or as otherwise directed by such a system.

The sensor (e.g., sensor 71, 72 shown in FIGS. 8A-8B, 9, and 10) of the security system may include multiple sensors or sub-sensors, such as where a position sensor includes both a global positioning sensor (GPS) as well as a wireless network sensor, which provides data that can be correlated with known wireless networks to obtain location information. Multiple sensors may be arranged in a single physical housing, such as where a single device includes movement, temperature, magnetic, and/or other sensors. Such a housing also may be referred to as a sensor or a sensor device. For clarity, sensors are described with respect to the particular functions they perform and/or the particular physical hardware used, when such specification is necessary for understanding of the implementations disclosed herein.

FIG. 10 shows an example sensor as disclosed herein. The sensor 71, 72 may include an environmental sensor 61, such as a passive infrared (PIR) sensor, temperature sensor, smoke sensor, carbon monoxide sensor, motion sensor, accelerometer, proximity sensor, magnetic field sensor, radio frequency (RF) sensor, light sensor, humidity sensor, or any other suitable environmental sensor, that obtains a corresponding type of information about the environment in which the sensor 71, 72 is located. A processor 64 may receive and analyze data obtained by the sensor 61, control operation of other components of the sensor 71, 72, and process communication between the sensor and other devices. In some implementations, the processor 64 may be the same as processor 200 shown in FIGS. 2A-2b and described above. The processor 64 may execute instructions stored on a computer-readable memory 65. The memory 65 or another memory in the sensor 71, 72 may also store environmental data obtained by the sensor 61. A communication interface 63, such as a Wi-Fi or other wireless interface, Ethernet or other local network interface, or the like may allow for communication by the sensor 71, 72 with other devices.

A user interface (UI) 62 may provide information (e.g., via a display device or the like) and/or receive input from a user of the sensor. The UI 62 may include, for example, a speaker to output an audible alarm and/or message when an event is detected by the sensor 71, 72. The speaker may output a message to an authorized user regarding the operational status (e.g., there are no security and/or environmental events, an operational issue has been detected, and/or a security event and/or environmental event has been detected) of the security system disclosed herein, when, for example, the user arrives at the building (e.g., the user's home, the user's office, or the like), or when the user exits the building. The speaker may output an audible message for a user to access information regarding the operational status of the security system, for example, when the user arrives at the building (e.g., a home, an office, or the like) via an application installed and/or accessible from an electronic device (e.g., device 75 illustrated in FIG. 8B and/or FIG. 11). Alternatively, or in addition, the UI 62 may include a light to be activated when an event is detected by the sensor 71, 72. The user interface may be relatively minimal, such as a limited-output display, or it may be a full-featured interface such as a touchscreen.

Components within the sensor 71, 72 may transmit and receive information to and from one another via an internal bus or other mechanism as will be readily understood by one of skill in the art. One or more components may be implemented in a single physical arrangement, such as where multiple components are implemented on a single integrated circuit. Sensors as disclosed herein may include other components, and/or may not include all of the illustrative components shown.

Sensors as disclosed herein may operate within a communication network, such as a conventional wireless network, and/or a sensor-specific network through which sensors may communicate with one another and/or with dedicated other devices. In some configurations one or more sensors may provide information to one or more other sensors, to a central controller, or to any other device capable of communicating on a network with the one or more sensors. A central controller may be general- or special-purpose. For example, one type of central controller is a home automation network that collects and analyzes data from one or more sensors within the home. Another example of a central controller is a special-purpose controller that is dedicated to a subset of functions, such as a security controller that collects and analyzes sensor data primarily or exclusively as it relates to various security considerations for a location. A central controller may be located locally with respect to the sensors with which it communicates and from which it obtains sensor data, such as in the case where it is positioned within a home that includes a home automation and/or sensor network. Faults and/or other issues with sensors may be reported to the central controller. If the communications network that the sensors and the central controller are part of experiences connectivity issues, data to authenticate users so as to allow entry, and/or arming and/or disarming of the security system may be stored at individual sensors that may serve as access points to the home and/or building. Alternatively or in addition, a central controller as disclosed herein may be remote from the sensors, such as where the central controller is implemented as a cloud-based system that communicates with multiple sensors, which may be located at multiple locations and may be local or remote with respect to one another.

Figure 11:
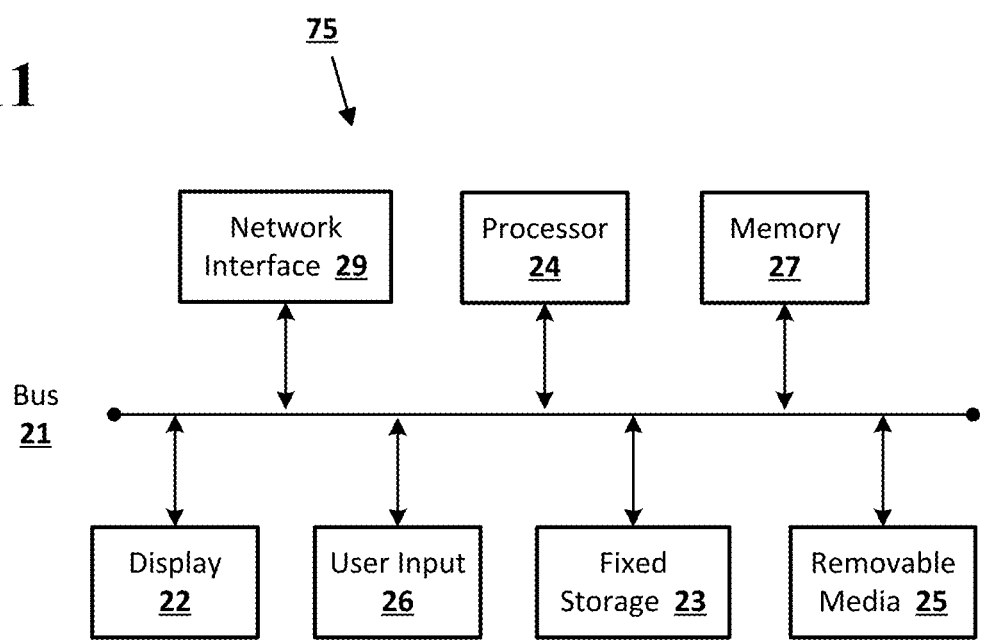
FIG. 11 shows an electronic device according to implementations of the disclosed subject matter.

Implementations of the presently disclosed subject matter may be implemented in and used with a variety of computing devices. FIG. 11 is an example computing device 75 suitable for implementing implementations of the presently disclosed subject matter (e.g., the device 75 shown in FIG. 8B). The device 75 may be used to implement a controller, a device including sensors as disclosed herein, or the like. Alternatively or in addition, the device 75 may be, for example, a desktop or laptop computer, or a mobile computing device such as a smart phone, smart watch, wearable computing device, tablet, key FOB, RFID tag, fitness band or sensor, or the like. The device 75 may include a bus 21 which interconnects major components of the device 75, such as a central processor 24, a memory 27 such as Random Access Memory (RAM), Read Only Memory (ROM), flash RAM, or the like, a user display 22 such as a display screen and/or lights (e.g., green, yellow, and red lights, such as light emitting diodes (LEDs) to provide the operational status of the security system to the user, as discussed above), a user input interface 26, which may include one or more controllers and associated user input devices such as a keyboard, mouse, touch screen, and the like, a fixed storage 23 such as a hard drive, flash storage, and the like, a removable media component 25 operative to control and receive an optical disk, flash drive, and the like, and a network interface 29 operable to communicate with one or more remote devices via a suitable network connection.

The bus 21 allows data communication between the central processor 24 and one or more memory components 25, 27, which may include RAM, ROM, and other memory, as previously noted. Applications resident with the device 75 are generally stored on and accessed via a computer readable storage medium.

The fixed storage 23 may be integral with the device 75 or may be separate and accessed through other interfaces. The network interface 29 may provide a direct connection to a remote server via a wired or wireless connection. The network interface 29 may provide a communications link with the network 70, sensors 71, 72, controller 73, and/or the remote system 74 as illustrated in FIGS. 8A-8B. The network interface 29 may provide such connection using any suitable technique and protocol as will be readily understood by one of skill in the art, including digital cellular telephone, radio frequency (RF), Wi-Fi, Bluetooth®, Bluetooth Low Energy (BTLE), near-field communications (NFC), and the like. For example, the network interface 29 may allow the device to communicate with other computers via one or more local, wide-area, or other communication networks, as described in further detail herein.

Various implementations of the presently disclosed subject matter may include or be embodied in the form of computer-implemented processes and apparatuses for practicing those processes. Implementations also may be embodied in the form of a computer program product having computer program code containing instructions embodied in non-transitory and/or tangible media, such as hard drives, USB (universal serial bus) drives, or any other machine readable storage medium, such that when the computer program code is loaded into and executed by a computer, the computer becomes an apparatus for practicing implementations of the disclosed subject matter. When implemented on a general-purpose microprocessor, the computer program code may configure the microprocessor to become a special-purpose device, such as by creation of specific logic circuits as specified by the instructions.

Implementations may be implemented using hardware that may include a processor, such as a general purpose microprocessor and/or an Application Specific Integrated Circuit (ASIC) that embodies all or part of the techniques according to implementations of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to implementations of the disclosed subject matter.

The foregoing description, for purpose of explanation, has been described with reference to specific implementations. However, the illustrative discussions above are not intended to be exhaustive or to limit implementations of the disclosed subject matter to the precise forms disclosed. Many modifications and variations are possible in view of the above teachings. The implementations were chosen and described in order to explain the principles of implementations of the disclosed subject matter and their practical applications, to thereby enable others skilled in the art to utilize those implementations as well as various implementations with various modifications as may be suited to the particular use contemplated.

The invention claimed is:

1. A method of detecting human movement with a device of a security system, the method comprising:
   generating, at a sensor of the device, a motion event signal in response to movement detected by the sensor;
   generating, at a processor of the device coupled to the sensor, a parameterized curve to represent the movement detected at the sensor based on the motion event signal;
   fitting, at the processor, the parameterized curve to a predetermined window of sensor data captured by the sensor that includes at least a portion of the motion event signal;
   determining, at the processor, a noise source signal magnitude estimate of a known noise based on the fitted parameterized curve to the predetermined window;
   determining, at the processor, a curve fit error based on the fitted parameterized curve to the predetermined window;
   determining, at the processor, a detection threshold value based on the curve fit error, the noise source signal magnitude estimate of the known noise, and zero or more noise magnitudes estimated at the processor from other noise sources;
   filtering, at the processor, noise from the motion event signal by subtracting the noise source signal magnitude estimate from the motion event signal;
   and determining, at the processor, that the filtered motion event signal correlates with human motion based on a comparison between a value of a point on the fitted parameterized curve and the detection threshold value, and raising the detection threshold value when the noise source signal magnitude estimate is based on a noise signal generated from an internal radio transmission of the device that includes the sensor.

2. The method of claim 1, wherein the generating the parameterized curve comprises:
   generating the parameterized curve using at least one from the group consisting of: low-order polynomials, and a sum of sinusoids over a predetermined frequency range.

3. The method of claim 1, wherein the fitting the parameterize curve comprises:
fitting, at the processor, the parameterized curve to the predetermined window using a least-squares optimization.

4. The method of claim 1, further comprising:
selecting, at the processor, the value of the point on the parameterized curve to be within the predetermined window.

5. The method of claim 1, further comprising:
raising the detection threshold value for a determined magnitude and time based on the noise source signal magnitude estimate.

6. The method of claim 1, wherein the determining the noise source signal magnitude estimate comprises:
determining, at the processor, that the noise source signal magnitude estimate corresponds to an electrostatic discharge signal detected by the sensor.

7. The method of claim 1, further comprising:
correlating, at the processor, the noise source signal magnitude estimate with a second data signal from a second sensor of the device.

8. The method of claim 7, further comprising:
correlating the noise source signal magnitude estimate with jarring of the sensor based on accelerometer data from the second sensor.

9. The method of claim 1, further comprising:
raising the detection threshold value, at the processor, when the noise source signal magnitude estimate is based on a signal obtained from an internal radio transmission of the device.

10. A system comprising:
a sensor of a device of a security system to generate a motion event signal in response to movement detected by the sensor; and
a processor of the device of the security system, coupled to the sensor, to generate a parameterized curve to represent the movement detected at the sensor based on the motion event signal, to fit the parameterized curve to a predetermined window of sensor data captured by the sensor that includes at least a portion of the motion event signal, to determine a noise source signal magnitude estimate of a known noise based on the fitted parameterized curve to the predetermined window, to determine a curve fit error based on the fitted parameterized curve to the predetermined window, to determine a detection threshold value based on the curve fit error, the noise source signal magnitude estimate of the known noise, and zero or more noise magnitudes estimated at the processor from other noise sources, to filter noise from the motion event signal by subtracting the noise source signal magnitude estimate from the motion event signal, to determine that the filtered motion event signal correlates with human motion based on a comparison between a value of a point on the fitted parameterized curve and the detection threshold value, and to raise the detection threshold value when the noise source signal magnitude estimate is based on a noise signal generated from an internal radio transmission of the device that includes the sensor.

11. The system of claim 10, wherein the processor generates the parameterized curve using at least one from the group consisting of: low-order polynomials, and a sum of sinusoids over a predetermined frequency range.

12. The system of claim 10, wherein the processor fits the parameterized curve to the predetermined window using a least-squares optimization.

13. The system of claim 10, wherein the value of the point on the parameterized curve is selected by the processor to be within the predetermined window.

14. The system of claim 10, wherein the processor raises the detection threshold value for a determined magnitude and time based on the noise source signal magnitude estimate.

15. The system of claim 10, wherein the noise source signal magnitude estimate corresponds to an electrostatic discharge signal detected by the sensor.

16. The system of claim 10, wherein the processor correlates the noise source signal magnitude estimate with a second data signal from a second sensor of the device.

17. The system of claim 16, wherein the second sensor is an accelerometer, and the noise source signal magnitude estimate is correlated by the processor with jarring of the sensor based on accelerometer data from the second sensor.

18. The method of claim 17, wherein the processor raises the detection threshold value when the noise source signal magnitude estimate is based on a signal obtained from an internal radio transmission of the device.

19. A system comprising:
a processor of a device of a security system to receive a motion event signal from a sensor of the device, to fit a parameterized curve to a predetermined window of sensor data captured by the sensor that includes the motion event signal, and to determine a curve fit error;
wherein the processor includes:
a dynamic threshold estimator to output a detection threshold value based on the determined curve fit error, a noise source signal magnitude estimate of a known noise in the motion event signal, and zero or more noise magnitude estimates from other noise sources, wherein the processor filters noise from the motion event signal by subtracting the noise source signal magnitude estimate from the motion event signal and raises the detection threshold value when the noise source signal magnitude estimate is based on a noise signal generated from an internal radio transmission of the device that includes the sensor;
and a detector to output a determined motion event based on a comparison between a value of a point on the fitted parameterized curve and the detection threshold value.

20. A method comprising:
receiving, at a processor of a device of a security system, a motion event signal from a sensor of the device;
fitting a parameterized curve to a predetermined window of sensor data captured by the sensor that includes the motion event signal, wherein the processor determines a curve fit error;
outputting, at a dynamic threshold estimator of the processor, a detection threshold value based on the determined curve fit error, a noise source signal magnitude estimate of a known noise in the motion event signal, and zero or more noise magnitude estimates from other noise sources,
filtering, at the processor, noise from the motion event signal by subtracting the noise source signal magnitude estimate from the motion event signal;
raising, at the processor, the detection threshold value when the noise source signal magnitude estimate is based on a noise signal generated from an internal radio transmission of the device that includes the sensor; and
outputting, at a detector of the processor, a determined motion event based on a comparison between a value of a point on the fitted parameterized curve and the detection threshold value.

* * * * *